(12) United States Patent
Petzelbauer et al.

(10) Patent No.: US 8,088,890 B2
(45) Date of Patent: Jan. 3, 2012

(54) PEPTIDES AND PEPTIDOMIMETIC COMPOUNDS, THE MANUFACTURING THEREOF AS WELL AS THEIR USE FOR PREPARING A THERAPEUTICALLY AND/OR PREVENTIVELY ACTIVE PHARMACEUTICAL COMPOSITION

(75) Inventors: Peter Petzelbauer, Vienna (AT); Sonja Reingruber, Vienna (AT); Rainer Henning, Uetliburg (CH)

(73) Assignee: Fibrex Medical Research & Development GmbH, Vienna (AT)

( * ) Notice: Subject to any disclaimer, the term of this patent is extended or adjusted under 35 U.S.C. 154(b) by 361 days.

(21) Appl. No.: 12/239,579

(22) Filed: Sep. 26, 2008

(65) Prior Publication Data
US 2010/0081787 A1    Apr. 1, 2010

(51) Int. Cl.
*A61K 38/04*    (2006.01)
*C07K 5/00*    (2006.01)
*C07K 7/00*    (2006.01)
*C07K 16/00*    (2006.01)
*C07K 17/00*    (2006.01)
(52) U.S. Cl. .................................................. 530/327
(58) Field of Classification Search .................. None
See application file for complete search history.

(56) References Cited

FOREIGN PATENT DOCUMENTS

| EP | 1 586 586 A2 |   | 10/2005 |
|----|--------------|---|---------|
| WO | 92/16221     |   | 10/1992 |
| WO | WO 95/24419  | * | 9/1995  |
| WO | WO 03/033515 | * | 4/2003  |
| WO | 2004/101600 A2 |  | 11/2004 |

OTHER PUBLICATIONS

H.J.C. Berendsen. A Glimpse of the Holy Grail? Science (1998) 282, pp. 642-643.*
Rudinger. In: Peptide Hormones, JA Parsons, Ed. (1976), pp. 1-7.*
SIGMA. Designing Custom Peptides. http://www.sigma-genosys.com/peptide_design.asp (Accessed Dec. 16, 2004), 2 pages.*
W.S. Messer, "Vasopressin and Oxytocin", web document updated Apr. 3, 2000; http://www.neurosci.pharm.utoledo.edu/MBC3320/vasopressin.htm; 5 pages.*
D.E. Smilek, et al. Proc. Natl. Acad. Sci. USA (1991) 88, pp. 9633-9637.*
Voet and J.G. Voet. Biochemistry, 2nd Edition.(1995), pp. 235-241.*
Hruby. Designing peptide receptor agonists and antagonists. Nature reviews. Drug Discovery. 2002. pp. 847-858.*
Abuchowski, et al "Effect of Covalent Attachment of Polyethylene Glycol on Immunogenicity and Circulating Life of Bovine Liver Catalase"; The Journal of Biological Chemistry vol. 252, No. 11 Issue of Jun. 10, 1977; pp. 3582-3586.
Reddy, "Controlled-release, pegylation, liposomal formulations: new mechanisms in the delivery of injectable drugs"; The Annals of Pharmacotherapy: vol. 34, No. 7 pp. 915-923.

Dejana, "Perspectives Series: Cell Adhesion in Vascular Biology, Endothelial Adherens Junctions: Implications in the Control of Vascular Permeability and Angiogenesis" J. Clin. Invest. vol. 98, No. 9 pp. 1949-1953; Nov. 1996.
Fukata, et al "Phosphorylation of Adducin by Rho-Kinase Plays a Crucial Role in Cell Motility" The Journal of Cell Biology, vol. 145, No. 2 pp. 347-361; Apr. 19, 1999.
Garcia, et al "Regulation of endothelial cell gap formation and barrier dysfunction: role of myosin light chain phosphorylation" J. Cell Physiol. vol. 163 No. 3 pp. 510-522; Jun. 1995.
Harris, et al "Effect of pegylation on pharmaceuticals" Nat Rev Drug Discov. vol. 2 No. 3 pp. 214-221; Mar. 2003.
Huang, et al "Interaction of PKC and NOS in signal transduction of microvascular hyperpermeability" Am J Physiol Heart Circ Physiol vol. 273 pp. 2442-2451; 1997.
Kita, et al "Characterization of a polyethylene glycol conjugate of recombinant human interferon-gamma" Drug Des Deliv. vol. 6 No. 3 pp. 157-167; Sep. 1990.
Knauf, et al "Relationship of Effective Molecular Size to Systemic Clearance in Rats of Recombinant Interleukin-2 Chemically Modified with Water-soluable Polymers" The Journal of Biological Chemistry, vol. 263 No. 29 pp. 15064-15070; Oct. 15, 2088.
Lee, et al "Synthesis, Characterization, and Pharmacokinetic Studies of PEGylated Glucagon-like Peptide-1" Bioconjugate Chem. vol. 16 pp. 377-382; 2005.
Lee, et al "Isolation, Characterization, and Stability of Positional Isomers of Mono-PEGylated Salmon Calcitonins" Pharmaceutical Research, vol. 16 No. 6, pp. 813-818 Jun. 1999; Springer Netherlands.
Goeckeler, et al "Phosphorylation of Myosin Light Chain Kinase by p21-activated Kinase PAK2" J. Biol. Chem. vol. 275 Issue 24, pp. 18366-18374 Jun. 16, 2000.
Lum, et al Regulation of vascular endothelial barrier function: Am J Physiol Lun Cell Mol Physiol vol. 267 Issue 3 pp. L223-L241, 1994.
Wojciak-Stothard, et al "Rac1 and RohA as regulators of endothelial phenotype and barrier function in hypoxia-induced neonatal pulmonary hypertension" Am J Physiol Lun Cell Mol Physiol vol. 290 pp. 1173-1182; 2006.

(Continued)

*Primary Examiner* — Marcela M Cordero Garcia
(74) *Attorney, Agent, or Firm* — Maschoff Gilmore & Israelsen

(57) ABSTRACT

Peptides, peptidomimetics and derivatives thereof of the general formula I:

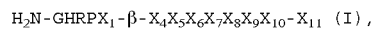

$H_2N\text{-}GHRPX_1\text{-}\beta\text{-}X_4X_5X_6X_7X_8X_9X_{10}\text{-}X_{11}$  (I), in which
$X_1$-$X_{10}$ denote one of the 20 genetically coded amino acids, wherein $X_8$, $X_9$ and $X_{10}$ may also denote a single chemical bond;
$X_{11}$ denotes $OR_1$ in which $R_1$ equals hydrogen or ($C_1$-$C_{10}$) alkyl $NR_2R_3$ with $R_2$ and $R_3$ are equal or different and denote hydrogen, ($C_1$-$C_{10}$) alkyl, or
a residue —W-$PEG_{5-60K}$, in which the PEG residue is attached via a suitable spacer W to the N-atom, or
a residue NH—Y—Z-$PEG_{5-60K}$, in which
Y denotes a chemical bond or a genetically coded amino acids from the group S, C, K or R and
Z denotes a spacer, via which a polyethylene glycol (PEG)-residue can be attached, and their physiologically acceptable salts, and
β denotes an amino acid, or a peptidomimetic element, which induces a bend or turn in the peptide backbone.

10 Claims, No Drawings

OTHER PUBLICATIONS

Ross, et al "Binding and Functional Studies with the Growth Hormone Receptor Antagonist, B2036-PEG (Pegvisomant), Reveal Effects of Pegylation and Evidence that it Binds to a Receptor Dimer" The Journal of Clinical Endocrinology & Metabolism vol. 86 No. 4; 2001.

Esposito, et al "PEGylation of growth hormone-releasing hormone (GRF) analogues" Advanced Drug Delivery Reviews vol. 55, Issue 10 pp. 1279-1291 Sep. 26, 2003.

Caliceti, et al "Pharmacokinetic and biodistribution of poly(ethylene glycol)—protein conjugates" Advanced Drug Delivery Reviews vol. 55 Issue 10 pp. 1261-1277 Sep. 26, 2003.

Tsutsumi, et al "Polyethylene glycol modification of interleukin-6 enhances its thrombopoietic activity" Journal of Controlled Release, vol. 33, Issue 3 pp. 447-451 Mar. 1995.

Seasholtz, et al "Rho as a Mediator of G Protein-Coupled Receptor Signaling" Molecular Pharmacology, vol. 55 pp. 949-956 1999.

Katoh, et al "Stress fiber organization regulated by MLCK and Rho-kinase in cultured human fibroblasts" Am J Physiol Cell Physiol vol. 280 Issue 6 pp. C1669-C1679; Jun. 2001.

Carbajal, et al "ROCK mediates thrombin's endothelial barrier dysfunction" Am J Physiol Cell Physiol vol. 279, pp. C195-C204 2000.

Tinsley, et al "Activated Neutrophils Induce Hyperpermeability and Phosphyorylation of Adherens Junction Proteins in Coronary Venular Endothelial Cells" The Journal of Biological Chemistry, vol. 274 No. 35 pp. 24930-24934 Aug. 27, 1999.

Toshima, et al "Cofilin Phosphorylation by Protein Kinase Testicular Protein Kinase 1 and its Role in Integrin-mediated Actin Reorganization and Focal Adhesion Formation" Molecular Biology of the Cell, vol. 12 pp. 1131-1145 Apr. 2001.

Amerongen, et al "Transient and Prolonged Increase in Endothelial Permeability Induced by Histamine and Thrombin: Role of Protein Kinases, Calsium, and RhoA" Circ. Res. 1998;83;1115-1123.

Grazia, et al "VE-Cadherin Regulates Endothelial Actin Activating Rac and Increasing Membrane Association of Tiam" Molecular Biology of the Cell, vol. 13 pp. 1175-1189 Apr. 2002.

Vincent, et al "VE-cadherin: adhesion at arm's length" Am J Physiol Cell Physiol vol. 286 pp. C987-C997 2004.

Wojciak-Stothard, et al "Rho GTPases and the regulation of endothelial permeability" Vascular Pharmacology vol. 30 Issues 4-5 pp. 187-199 Nov. 2002.

* cited by examiner

PEPTIDES AND PEPTIDOMIMETIC COMPOUNDS, THE MANUFACTURING THEREOF AS WELL AS THEIR USE FOR PREPARING A THERAPEUTICALLY AND/OR PREVENTIVELY ACTIVE PHARMACEUTICAL COMPOSITION

The present invention relates to peptides and peptidomimetic compounds, to the manufacturing thereof as well as to their use for preparing a therapeutically and/or preventively active drug and to such a pharmaceutical drug.

EP1586586 describes the use of peptides from the sequence of fibrin possessing anti-inflammatory effects.

Said effect may be based on the fact that the fibrin and fibrin fragments generated during the breakdown thereof bind to endothelial cells via its neo-N-terminus of the Bbeta-chain and to cells in the bloodstream via the sequence of the Aalpha-chain, thereby leading to the adhesion and transmigration of these cells into the tissue. The binding partner of the fibrin and fibrin fragments to the endothelial cells is the protein vascular endothelial (VE) cadherin, which is expressed exclusively in the adherens junction between neighboring endothelial cells. The peptides according to the invention block this interaction and thereby counteract the transmigration of blood cells. The natural defense against infections by the leukocytes in the blood is not adversely affected, however. Thus, the composition of the same, such as granulocytes, lymphocytes and monocytes, remains unaffected so that the natural defense process is maintained.

Fibrinogen is produced in the liver and, in this form, is biologically inactive and normally is provided in the blood at concentrations of around 3 g/l. Proteolytic cleavage of the proenzyme prothrombin results in the formation of thrombin, which cleaves off the fibrinopeptides A and B from the fibrinogen. In this way, fibrinogen is transformed into its biologically active form. Fibrin and fibrin cleavage products are generated.

Thrombin is formed whenever blood coagulation is activated, i.e. with damage to the tissue, be it of inflammatory, traumatic or degenerative genesis. The formation of fibrin as mediated by thrombin is basically a protective process aimed at quickly sealing any defects caused to the vascular system. However, the formation of fibrin also is a pathogenic process. The appearance of a fibrin thrombus as the triggering cause of cardiac infarction is one of the most prominent problems in human medicine.

The role which fibrin plays during the extravasation of inflammatory cells from the bloodstream into the tissue, which, on the one hand, is a desired process for the defense against pathogenic microorganisms or tumor cells in the tissue, but, on the other hand, is a process which, by itself, induces or prolongs damage done to the tissue, has so far not been examined at all or not to a sufficient extent. Fibrin binds to endothelial cells via its neo-N-terminus of Bbeta by means of the sequence to Bbeta and to cells in the bloodstream by means of the sequence Aalpha, thereby leading to the adhesion and transmigration of cells into the tissue.

By way of the mechanism described above the peptides or proteins according to the invention may prevent the adhesion of cells from the bloodstream to endothelial cells of the vascular wall and/or their subsequent transmigration from the blood into the tissue.

One of the principal abnormalities associated with acute inflammatory disease is the loss of endothelial barrier function. Structural and functional integrity of the endothelium is required for maintenance of barrier function and if either of these is compromised, solutes and excess plasma fluid leak through the monolayer, resulting in tissue oedema and migration of inflammatory cells. Many agents increase monolayer permeability by triggering endothelial cell shape changes such as contraction or retraction, leading to the formation of intercellular gaps (Lum & Malik, Am. J. Physiol. 267: L223-L241 (1994). These agents include e.g thrombin, bradykinin and vascular endothelial growth factor (VEGF).

Hyperpermeability of the blood vessel wall permits leakage of excess fluids and protein into the interstitial space. This acute inflammatory event is frequently allied with tissue ischemia and acute organ dysfunction. Thrombin formed at sites of activated endothelial cells (EC) initiates this microvessel barrier dysfunction due to the formation of large paracellular holes between adjacent EC (Carbajal et al, *Am J Physiol Cell Physiol* 279: C195-C204, 2000). This process features changes in EC shape due to myosin light chain phosphorylation (MLCP) that initiates the development of F-actin-dependent cytoskeletal contractile tension (Garcia et al, *J Cell Physiol*. 1995; 163:510-522 Lum & Malik, Am J Physiol Heart Circ Physiol. 273(5): H2442-H2451. (1997).

Thrombin-induced endothelial hyperpermeability may also be mediated by changes in cell-cell adhesion (Dejana J. Clin. Invest. 98: 1949-1953 (1996). Endothelial cell-cell adhesion is determined primarily by the function of vascular endothelial (VE) cadherin (cadherin 5), a Ca-dependent cell-cell adhesion molecule that forms adherens junctions. Cadherin 5 function is regulated from the cytoplasmic side through association with the accessory proteins b-catenin, plakoglobin (g-catenin), and p120 that are linked, in turn, to a-catenin (homologous to vinculin) and the F-actin cytoskeleton.

VE-cadherin has emerged as an adhesion molecule that plays fundamental roles in microvascular permeability and in the morphogenic and proliferative events associated with angiogenesis (Vincent et al, Am J Physiol Cell Physiol, 286 (5): C987-C997 (2004). Like other cadherins, VE-cadherin mediates calcium-dependent, homophilic adhesion and functions as a plasma membrane attachment site for the cytoskeleton. However, VE-cadherin is integrated into signaling pathways and cellular systems uniquely important to the vascular endothelium. Recent advances in endothelial cell biology and physiology reveal properties of VE-cadherin that may be unique among members of the cadherin family of adhesion molecules. For these reasons, VE-cadherin represents a cadherin that is both prototypical of the cadherin family and yet unique in function and physiological relevance. A number of excellent reviews have addressed the contributions of VE-cadherin to vascular barrier function, angiogenesis, and cardiovascular physiology.

Evidence is accumulating that the VE-cadherin-mediated cell-cell adhesion is controlled by a dynamic balance between phosphorylation and dephosphorylation of the junctional proteins including cadherins and catenins. Increased tyrosine phosphorylation of b-catenin resulted in a dissociation of the catenin from cadherin and from the cytoskeleton, leading to a weak adherens junction (AJ). Similarly, tyrosine phosphorylation of VE-cadherin and b-catenin occurred in loose AJ and was notably reduced in tightly confluent monolayers (Tinsley et al., J Biol Chem, 274, 24930-24934 (1999).

In addition the correct clustering of VE-cadherin monomers in adherens junctions is indispensable for a correct signalling activity of VE-cadherin, since cell bearing a chimeric mutant (IL2-VE) containing a full-length VE-cadherin cytoplasmic tail is unable to cause a correct signalling despite its ability to bind to beta-catenin and p120 (Lampugnani et al, Mol. Biol. of the Cell, 13, 1175-1189 (2002).

Rho GTPases are a family of small GTPases with profound actions on the actin cytoskeleton of cells. With respect to the functioning of the vascular system they are involved in the regulation of cell shape, cell contraction, cell motility and cell adhesion. The three most prominent family members of the Rho GTPases are RhoA, Rac and cdc42. Activation of RhoA induces the formation of f-actin stress fibres in the cell, while Rac and cdc42 affect the actin cytoskeleton by inducing membrane ruffles and microspikes, respectively (Hall, *Science*, 279:509-514.1998). While Rac and cdc42 can affect MLCK activity to a limited extent via activation of protein PAK (Goeckeler et al. J. Biol. Chem., 275, 24, 18366-18374 (2000), RhoA has a prominent stimulatory effect on actin-myosin interaction by its ability to stabilize the phosphorylated state of MLC (Katoh et al., *Am. J. Physiol. Cell. Physiol.* 280, C1669-C1679 (2001). This occurs by activation of Rho kinase that in its turn inhibits the phosphatase PP1M that hydrolyses phosphorylated MLC. In addition, Rho kinase inhibits the actin-severing action of cofilin and thus stabilizes f-actin fibres (Toshima et al., *Mol. Biol. of the Cell.* 12, 1131-1145 (2001). Furthermore, Rho kinase can also be involved in anchoring the actin cytoskeleton to proteins in the plasma membrane and thus may potentially act on the interaction between junctional proteins and the actin cytoskeleton (Fukata et al. *Cell Biol* 145:347-361 (1999).

Thrombin can activate RhoA via Gα12/13 and a so-called guanine nucleotide exchange factor (GEF) (Seasholtz et al; Mol: Pharmacol. 55, 949-956 (1999). The GEF exchanges RhoA-bound GDP for GTP, by which RhoA becomes active. By this activation RhoA is translocated to the membrane, where it binds by its lipophilic geranyl-geranyl-anchor.

RhoA can be activated by a number of vasoactive agents, including lysophosphatidic acid, thrombin and endothelin. The membrane bound RhoA is dissociated from the membrane by the action of a guanine dissociation inhibitor (GDI) or after the action of a GTPase-activating protein (GAP). The guanine dissociation inhibitors (GDIs) are regulatory proteins that bind to the carboxyl terminus of RhoA.

GDIs inhibit the activity of RhoA by retarding the dissociation of GDP and detaching active RhoA from the plasma membrane. Thrombin directly activates RhoA in human endothelial cells and induces translocation of RhoA to the plasma membrane. Under the same conditions the related GTPase Rac was not activated. Specific inhibition of RhoA by C3 transferase from *Clostridium botulinum* reduced the thrombin-induced increase in endothelial MLC phosphorylation and permeability, but did not affect the transient histamine-dependent increase in permeability (van Nieuw Amerongen et al. *Circ Res.* 1998; 83:1115-11231 (1998). The effect of RhoA appears to be mediated via Rho kinase, because the specific Rho kinase inhibitor Y27632 similarly reduced thrombin-induced endothelial permeability.

Rac1 and RhoA have antagonistic effects on endothelial barrier function. Acute hypoxia inhibits Rac1 and activates RhoA in normal adult pulmonary artery endothelial cells (PAECs), which leads to a breakdown of barrier function (Wojciak-Stothard and Ridley, Vascul Pharmacol., 39:187-99 (2002). PAECs from piglets with chronic hypoxia induced pulmonary hypertension have a stable abnormal phenotype with a sustained reduction in Rac1 and an increase in RhoA activitity. These activities correlate with changes in the endothelial cytoskeleton, adherens junctions and permeability. Activation of Rac1 as well as inhibition of RhoA restored the abnormal phenotype and permeability to normal (Wojciak-Stothard et al., Am. J. Physiol, Lung Cell Mol. Physiol. 290, L1173-L1182 (2006).

Substances that active Rac1 and reduce RhoA activity to a level that is observed in endothelial cells in normal and stable conditions can therefore be expected to reduce endothelial hyperpermeability and have a beneficial therapeutic effect in a number of diseases. Preferably this effect is caused by a stabilization of the clustering of VE-cadherin in the adherens junction. An important component of the intracellular complex of proteins linked to VE-cadherin is fyn, a kinase which is a member of the src tyrosine kinases. The binding of the compounds which are subject to this invention to VE-cadherin cause a dissociation of fyn from VE-cadherin, which in turn leads to deactivation of thrombin induced active RhoA.

WO9216221 describes polypeptides which are covalently linked to long-chain polymers, as for instance methoxy-polyethylene glycol (PEG). The binding of polypeptides to such polymers frequently results in a prolongation of the biological half-life of these polypeptides and delays their renal excretion. A summary of these properties may be found in Davis et al., Polymeric Materials Pharmaceuticals for Biomedical Use, pp. 441-451 (1980) The addition of PEG-groups exerts this effect in a way proportional to the molecular weight of the PEGylated peptide, as, up to a certain size of the molecule, the glomular filtration rate is inversely proportional to the molecular weight.

WO2004/101600 also describes new poly(ethylene glycol)-modified compounds and their use, in particular with emphasis on modified peptides activating the erythropoietin receptor. Further examples for the covalent modification of peptides and proteins PEG residues are interleukins (Knauf et al., J. Biol. Chem. 1988, 263, 15064; Tsutumi et al., J. Controlled Release 1995, 33, 447), Interferons (Kita et al., Drug Delivery Res. 1990, 6 157), Catalase (Abuchowski et al., J. Biol. Chem. 1997, 252, 3582). A review of the prior art may be found in Reddy, Ann. of Pharmacotherapy, 2000, 34, 915.

A prolonged biological half-life is advantageous for various therapeutic uses of peptides. This is in particular true in cases of chronic diseases where the administration of the active agent over a prolonged period of time is indicated. With such indications this may improve the patient's compliance, as applying the active agent once a day will for instance be accepted more easily than continuous infusion. Apart from increasing the molecular mass by covalent modification, a prolongation of the persistency of polypeptides may be obtained by modifying them in such a way that their degradation by proteolytic enzymes (e.g. exo- or endoproteases or peptidases) is prevented.

Using various examples it has been shown that it is necessary to customize the appropriate modification for each peptide so as to prevent a significant influence on the pharmacodynamic effect as compared to the unmodified peptide. In this context the following may be referred to: Calcitonin (Lee et al. Pharm. Res. 1999, 16, 813), Growth Hormone Releasing Hormone (Esposito et al., Advanced Drug Delivery Reviews, 2003, 55, 1279), Glucagon like peptide 1 (Lee et al., Bioconjugate Res. 2005, 16, 377), as well as the growth hormone-receptor antagonist Pegvisomant (Ross et al., J. Clin. Endocrin. Metab. 2001, 86, 1716). The reviews by Caliceti and Veronese (Adv. Drug Deliv. Rev. 2003, 55 1261) and by Harris and Chess (Nature Rev. Drug Discovery 2003, 2, 214) discuss that in case of designing peptide- or protein-PEG-conjugates it is necessary to take into consideration the structure of the original substance, the molecular weight of the peptide and the polymer, the number of conjugated polymer chains as well as the linker chemistry, so as to obtain an effective peptide-PEG-conjugate.

Surprisingly it has now been found that peptides and peptidomimetics derived from the chain of the Bbeta(15-42)

fibrin fragment, in which one or amino acids have been removed and which instead contain an amino acid or a peptidomimetic element promoting a bend or turn in the peptide backbone, as well as derivatives modified at the C-terminal end of the peptide sequence also have strong anti-inflammatory and endothelium stabilizing effects. The same applies to peptides, peptidomimetics and derivatives thereof, the modification of which prevents their destruction by proteases or peptidases, as well as to peptide-PEG-conjugates and peptidomimetic-PEG-conjugates generally derived from the basic sequence of the Bbeta(15-42)fibrin fragment containing such turn-inducing elements Thus the invention relates peptidomimetics which are derived from the chain of the Bbeta(15-42)-fibrin fragment and wherein one or several of the amino acids of the sequence have been omitted and certain other amino acids residues of this chain substituted by genetically encoded or not genetically encoded amino acids or peptidomimetics, which have the property of inducing a bend or turn in the peptide backbone. They may exist as free peptides or may be modified at the C-terminal end and/or being linked to a polyethylene glycol (PEG)-polymer, and have anti-inflammatory and/or endothelium stabilizing effects. Esters or amides may for instance be taken into consideration as C-terminal derivatives.

The inventive compounds may have conservative substitutions of amino acids as compared to the natural sequence of fibrin of the warm blooded animals to be treated in one or several positions. A conservative substitution is defined as the side chain of the respective amino acid being replaced by a side chain of similar chemical structure and polarity, the side chain being derived from a genetically coded or not genetically coded amino acid. Families of amino acids of this kind having similar side chains are known in the art. They comprise for instance amino acids having basic side chains (lysins, arginins, histidine), acidic side chains (aspartic acid, glutamic acid), uncharged polar side chains (glycine, aspartamic acid, glutamine, serine, threonine, tyrosine, cysteine), non-polar side chains (alanine, valine, leucine, isoleucine, proline, phenylalanine, methionine, tryptophan), beta-branched side chains (threonine, valine, isoleucine) and aromatic side chains (tyrosine, phenylalanine, tryptophane, histidine). Such conservative substitutions of side chains may preferably be carried out in non-essential positions. In this context, an essential position in the sequence is one wherein the side chain of the relevant amino acid is of significance for its biological effect.

The invention in particular concerns peptides, peptidomimetics and derivatives thereof of the following general formula I:

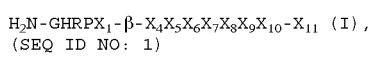
(SEQ ID NO: 1)

in which $X_1$-$X_{10}$ denote one of the 20 genetically coded amino acids, wherein $X_8$, $X_9$ and $X_{10}$ individually or jointly may also denote a single chemical bond and in which $X_4$ and $X_5$ may denote a suitable spacer of a lengths similar to 2 amino acid residues and $X_1$ may also denote a single chemical bond $X_{11}$ denotes $OR_1$ in which $R_1$ equals hydrogen or $(C_1$-$C_{10})$ alkyl, $NR_2R_3$ with $R_2$ and $R_3$ are equal or different and denote hydrogen, $(C_1$-$C_{10})$ alkyl or a residue —W-$PEG_{5-60K}$, in which the PEG residue is attached via a suitable spacer W to the N-atom, or a residue

NH—Y—Z-$PEG_{5-60K}$, in which

Y denotes a single chemical bond or a genetically coded amino acids from the group S, C, K or R and in which Z denotes a spacer, via which a polyethylene glycol (PEG)-residue can be attached, as well as their physiologically acceptable salts, and in which additionally β denotes an amino acid, whether genetically coded or not, or a peptidomimetic element, which have the additional property of inducing a bend or turn in the peptide backbone. Such amino acids include without limitation L-proline, D-proline, L-hydroxyproline, D-hydroxyproline, L-(O-benzyl)-hydroxyproline, D-(O-benzyl)-hydroxyproline, L-(O -tert. butyl)-hydroxyproline, 4-(O-2-naphtyl)-hydroxyproline, 4-(O-2-naphtyl-methyl)-hydroxyproline, 4-(O-phenyl)-hydroxyproline, 4-(4-phenyl-benzyl)-proline, cis-3-phenyl-proline, cis-4-phenyl-proline, trans-4-phenyl-proline, cis-5-phenyl-proline, trans-5-phenyl-proline, 4-benzyl-proline, 4-bromobenzyl-proline, 4-cyclohexyl-proline, 4-fluor-proline, L-tetrahydroisoquinoline-2-carboxylic acid (L-Tic), all diastereomers of octahydro-indole-2-carboxylic acid (Oic), and all diastereomers of 1-aza-bicyclo [3,3,0]octane-2-carboxylic acid. Additional amino acids having the turn-inducing property are know to one skilled in the art and are compounds of formula I containing them also subject of this invention.

Peptidomimetic elements pertaining to this invention are residues, which are able to replace one or several amino acids of a peptide chain and which also have the additional property of inducing a bend or turn in the peptide backbone. Several such residues have for instance been described in the patent application WO2005/056577, in which they were used for the preparation of peptidic HIV inhibitors.

A selection of useful peptidomimetic elements for the purpose of this invention are, without limitation the following:

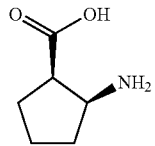

cis-2-aminocyclopentane carboxylic acid (cis-Acpc)

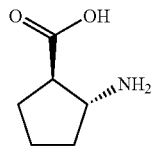

(1R,2R)-(2-aminocyclopentane carboxylic acid ((1R,2R)-Acpc)

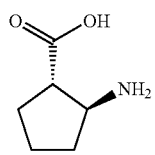

(1S,2S)-(2-aminocyclopentane carboxylic acid ((1S,2S)-Acpc)

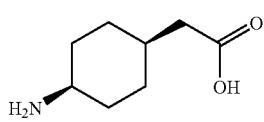

1-aminomethyl-cyclohexane acetic acid (1-Achc)

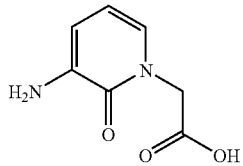

3-amino-1-carboxymethyl-pyridin-2-one (Acpo)

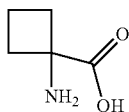

1-amino-cyclobutane-carboxylic acid (1-Acbc)

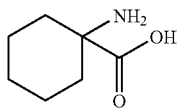

1-amino-cyclohexane-carboxylic acid (1-Achc)

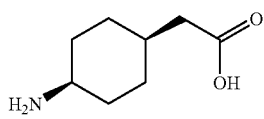

cis-4-amino-cyclohexane-acetic acid (4-Acha)

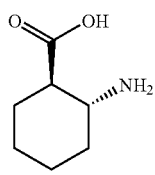

(1R,2R)-2-aminocyclohexane carboxylic acid ((1R,2R)-Achc)

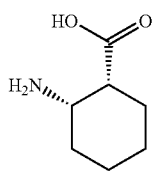

(1R,2S)-2-aminocyclohexane carboxylic acid ((1R,2S)-Achc)

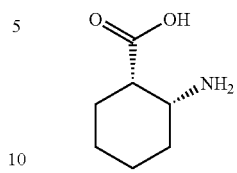

(1S,2R)-2-aminocyclohexane carboxylic acid ((1S,2R)-Achc)

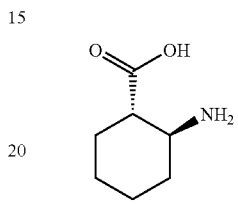

(1S,2S)-2-aminocyclohexane carboxylic acid ((1S,2S)-Achc)

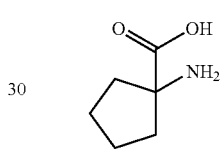

1-amino-cyclopentane carboxylic acid (1-Acpec)

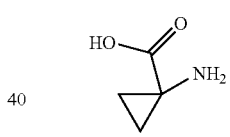

1-amino-cyclopropane carboxylic acid (1-Acprc)

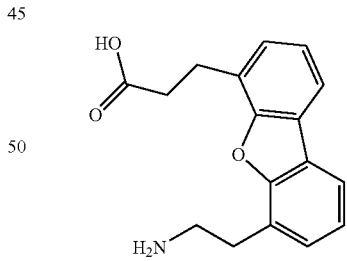

4-(2-aminoethyl)-6-dibenzofuranpropionic acid (Aedfp)

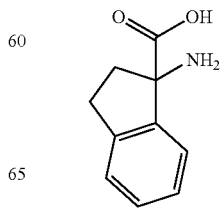

(R,S)-1-aminoindane-1-carboxylic acid (1-Aic)

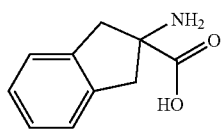

2-aminoindane-2-carboxylic acid (2-Aic)

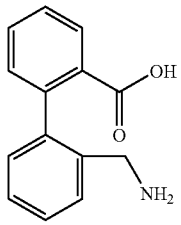

2'-(aminomethyl)-biphenyl-2-carboxylic acid (Ambc)

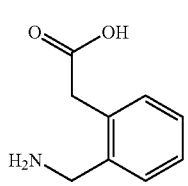

2-aminomethyl-phenylacetic acid (Ampa)

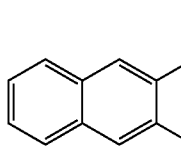

3-amino-2-naphthoic acid (Anc)

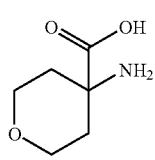

4-amino-tetrahydropyran-4-carboxylic acid (Atpc)

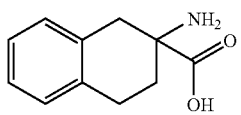

(R,S)-2-aminotetraline-2-carboxylic acid (2-Atc)

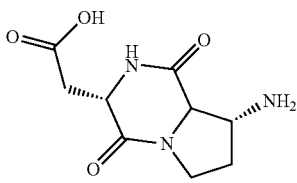

(2S,6S,9S)-6-amino-2-carboxymethyl-3,8-diazabicyclo-[4,3,0]-nonane-1,4-dione (Acdn)

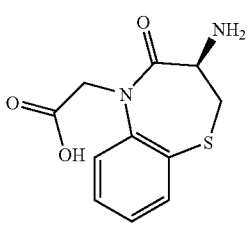

(R)-3-amino-5-carboxymethyl-2,3-dihydro-1,5-benzothiazepin-4(5H)-one (Acbt)

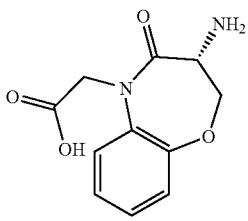

(S)-3-amino-5-carboxymethyl-2,3-dihydro-1,5-benzoxazepin-4(5H)-one (Acbo)

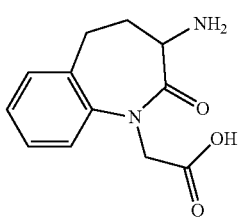

(R,S)-3-amino-1-carboxymethyl-2,3,4,5-tetrahydro-1H-[1]-benzazepin-2-one (1-Acmb)

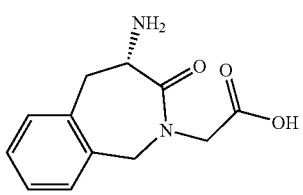

(S)-4-amino-2-carboxymethyl-1,3,4,5-tetrahydro-2H-[2]-benzazepin-3-one (2-Acmb)

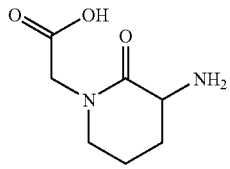

(R,S)-3-amino-1-carboxymethyl-valerolactame (Acmv)

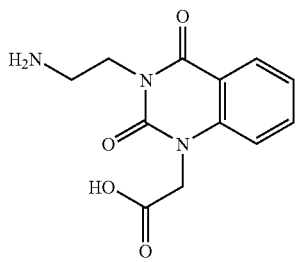

3-(2-aminoethyl)-1-carboxymethyl-quinazoline-2,4-dione (Acq)

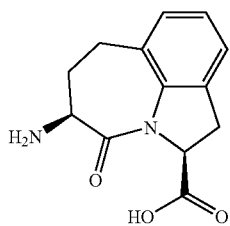

(2S,5S)-5-amino-1,2,4,5,6,7-hexahydro-azepino[3,2,1-hi]-indole-4-one-2-carboxylic acid (Haic)

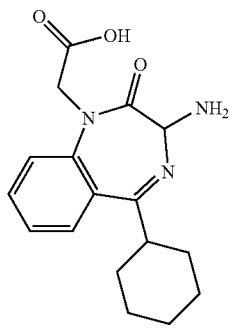

(R,S)-3-amino-N-1-carboxymethyl-2-oxo-5-cyclohexyl-1,4-benzodiazepine (Accb)

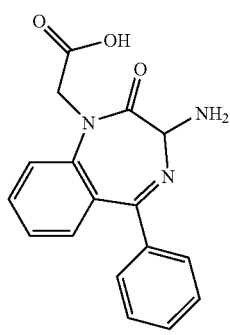

(R,S)-3-amino-N-1-carboxymethyl-2-oxo-5-phenyl-1,4-benzodiazepine (Acpb)

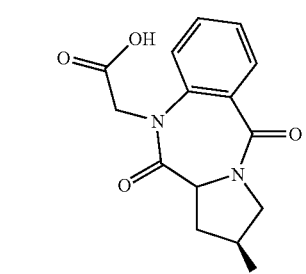

(2S,11aS)-2-amino-10-carboxymethyl-1,2,3,11a-tetrahydro-10H-pyrrolo[2,1-c][1,4]-benzodiazepine-5,11-dione (PBD)

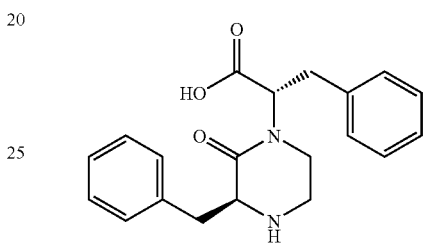

(2S,3'S)-2-(4'-(3'-benzyl-2'-oxo-piperazin-1-yl))-3-phenyl-propionic acid (Bppp)

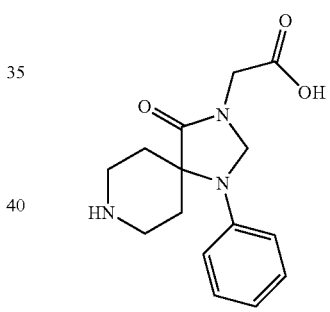

3-carboxymethyl-1-phenyl-1,3,8-triazaspiro[4.5]decan-4-one (Cptd)

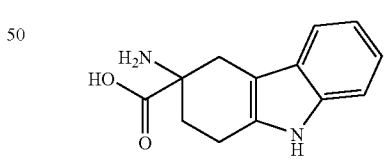

(R,S)-3-amino-9-Boc-1,2,3,4-tetrahydro-carbazole-3-carboxylic acid (Thc)

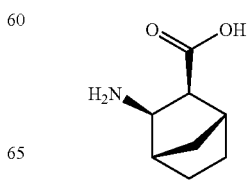

3-exo-amino-bicyclo[2.2.1]heptane-2-exo-carboxylic acid (Abhc)

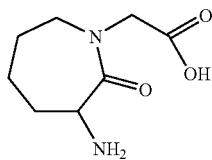

(3S)-3-Amino-1-carboxymethyl-caprolactam (Accl)

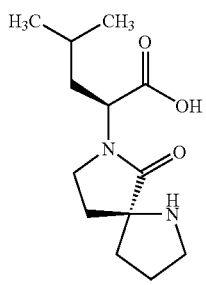

(S,S)-(ProLeu)spirolactamePhe (PLSP)

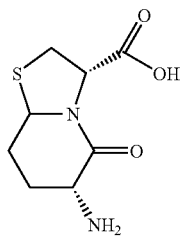

2-Oxo-3-amino-7-thia-1-azabicyclo[4.3.0]nonane-9-carboxylich acid (BTD)

Preferred subject of this invention are compounds of the general formula I, in which:
$X_1$ denotes L, I, S, M or A, or a single, chemical bond
$X_4$ denotes L, I, S, M or A,
$X_2$ denotes E or D,
$X_3$ denotes R or K
$X_5$, $X_6$, $X_7$ denote A, G, S, or L
$X_4$ and $X_5$ jointly denote a suitable spacer of a similar chain length as 2 amino acid residues
$X_8$ denotes G, A or L or a single chemical bond,
$X_9$ denotes Y, F, H or a single chemical bond
$X_{10}$ denotes R, K or a single chemical bond and in which
β and $X_{11}$ have the meaning described above
as well as their physiologically acceptable salts.

Especially preferred subject of this invention are compounds of the general formula II,

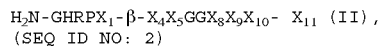

in which
$X_1$ denotes either L, I, A or a single chemical bond
$X_4$ denotes L, I, S, M or A,
$X_5$ denote A, G, S, or L, or
$X_4$ and $X_5$ jointly denote a suitable spacer of a similar chain length as 2 amino acid residues, $X_8$, $X_9$, $X_{10}$ and $X_{11}$ have the meaning described above for formula I and their physiologically acceptable salts.

Most highly preferred subjects of the invention are compounds of the general formula II, in which
$X_1$ denotes either L, I, A or a single chemical bond
$X_4$ denotes I
$X_5$ denotes S,
$X_{11}$ denotes OH, $OR_2$ or $NR_2R_3$, where $R_2$ and $R_3$ are equal or different and denote hydrogen or ($C_1$-$C_{10}$) alkyl, or a residue
$C(NR_2R_3)$—(S-succinimido)-($PEG_{5-40K}$), in which the succinimide residue is linked to the sulphur atom of the cysteine residue via carbon atom 3 of the succinimide ring,
as well as their physiologically acceptable salts.

In the above formulas I and II the following letters represent amino acid residues in accordance with the general annotation for proteins and peptides: pPhenylalanine is F, leucine is L, isoleucine is I, methionine is M, valine is V, serine is S, proline is P, threonine is T, alanine is A, tyrosine is Y, histidine is H, glutamine is Q, asparagine is N, lysine is K, aspartic acid is D, glutamic acid is E, cysteine is C, tryptophan is W, arginine is R, glycine is G.

The amino acid residues in the compounds of Formula I may either be present in their D or their L configuration.

The term peptide refers to a polymer of these amino acids, which are linked via an amide linkage.

"Physiologically acceptable" means that salts are formed with acids or bases the addition of which does not have undesirable effects when used for humans. Preferable are salts with acids or bases the use of which is listed for use with warm blooded animals, in particular humans, in the US Pharmacopoeia or any other generally recognized pharmacopoeia.

PEG stands for a polyethylene glycol residue having a molecular weight of between 5.000 and 60.000 Dalton, this molecular weight being the maximum of a molecular weight distribution, so that individual components of the mixture may have a higher or lower molecular weight.

The invention furthermore concerns processes for the production of the peptides and peptide derivatives of general Formula (I), characterized in that, either (A) the first amino acid at the C-terminal end of the respective sequence is linked to a polymeric resin via a suitable cleavable spacer, the subsequent amino acids or peptidomimetic elements, optionally containing suitable protective groups for functional groups, are linked step by step according to methods known in the art, the finished peptide is cleaved off the polymeric resin according to suitable methods known in the art, the protective groups, if present, are cleaved off by suitable methods and the peptide or peptide derivative is purified according to suitable methods, or (B) a PEG-group having a desired molecular weight is linked to a polymeric resin via a suitable spacer, the first amino acid at the N-terminal end of the peptide is linked using suitable methods, the remaining steps being the same as described in (A), or (C) a lysine residue, containing a suitable protective group at the ε-amino group is linked to a suitable polymeric resin via a suitable spacer using suitable methods, the peptide chain is synthesized as described in (A), following cleavage from the polymeric resin and purification, if necessary, the protective group at the ε-amino group is cleaved off using suitable methods, a PEG group having a desired molecular weight is linked to the ε-amino group using a suitable activated reagent, the optionally remaining protective groups are cleaved off and the final product is purified using suitable methods, or (D) a peptide containing a cysteine residue is reacted with a PEG-maleimide to form compounds of Formula (II).

Suitable processing steps following (A), (B) or (C) as well as suitable reagents are for instance described in document WO 2004/101600.

Embodiments of the respective processing steps are not new per se and will be clear to an experienced specialist in the field of organic synthesis.

Processes for linking a PEG-residue to a peptide chain will be known to the skilled artisan. For instance, a cysteine (C)-residue may be reacted with PEG-maleimide, resulting in a succinimide residue as spacer for residue Z. A further possibility is reacting an optionally activated C-terminal carboxy residue with an aminoalkyl-substituted PEG residue. A further possibility is the introduction of a PEG residue by reacting an aldehyde-substituted PEG residue with the $\epsilon$-amino function of a lysine residue. Activated PEG reagents having suitable spacers and reactive groups may for instance be obtained from NOF Corporation (Tokyo, Japan).

The substances according to the invention and the use of the substances according to the invention for the production of a pharmaceutical drug are of particular significance for the production of a pharmaceutical drug for the therapy of diseases resulting from the tissue-damaging effect of white blood cells, or wherein the integrity and full physiological integrity of the layer of endothelial cells lining the blood vessels is impaired.

Diseases belonging to this group are those in context with autoimmunity, as for instance collagenosis, rheumatic diseases, inflammatory bowel diseases like Morbus Crohn or Colitis ulcerosa, psoriasis and psoriatic rheumatoid arthritis, and post/parainfectious diseases as well as diseases caused by a graft-versus-host reaction. A healing effect takes place as this medical drug blocks the migration of the white blood cells into the tissue. Thus the white blood cells remain in the blood stream and cannot cause an autoreactive effect harmful to the tissue. This effect of the inventive substances is furthermore important for the treatment of shock conditions, in particular in case of septic shock triggered by infection with gram-positive or gram-negative bacterial pathogens as well as viral infections and haemorrhagic shock caused by heavy loss of blood because of severe injuries or bacterial or viral infections.

The inventive substances may generally be used in situations that can be described with the terms "Systemic Inflammatory Response Syndrome (SIRS)", "Acute Respiratory Distress Syndrome (ARDS)", "Capillary Leak Syndrome (CLS)" and organ- or multiorgan failure, respectively.

Associated with a pharmaceutical drug for the therapy and/or prevention of rejection reactions of organ transplants there is a healing effect as this pharmaceutical drug prevents the migration of white blood cells from the blood stream into the donor organ, and the donor organ can therefore not be destroyed for instance by autoreactive lymphocytes.

Associated with a pharmaceutical drug for the therapy and/or prevention of arteriosclerosis there is a healing and/or preventive effect as this pharmaceutical drug blocks the migration of lymphocytes and monocytes into the wall of the tissue and thus the activation of the cells of the tissue wall. Thus the progress of arteriosclerosis is minimized or stopped, the progredience of arteriosclerotic plaque resulting therefrom is inhibited, causing the arteriosclerosis to recede.

Associated with a pharmaceutical drug for the therapy and/or prevention of reperfusion trauma following surgically or pharmaceutically induced re-supply with blood, e.g. following percutaneous coronary intervention, stroke, vessel surgery, cardiac bypass surgery and organ transplants, there is a healing and/or preventive effect as this pharmaceutical drug inhibits the migration of lymphocytes, neutrophils and monocytes into the wall of the vessel. Reperfusion trauma is caused by a lack of oxygen/acidosis of the cells of the vessel during its re-supply with blood, leading to their activation and/or damage. Because of this, lymphocytes, neutrophils and monocytes adhere to the vessel wall and migrate into it. Blocking the adherence and migration of lymphocytes, neutrophils and monocytes in the vessel wall causes the hypoxy/acidosis-induced damage to abate, without the subsequent inflammatory reaction causing a permanent damage to the vessel. The endothelium-stabilizing effect of the inventive compounds furthermore prevents the formation of oedemas as well as any further damage to the organs supplied via the respective blood vessels.

Associated with a pharmaceutical drug for the therapy and/or prevention of arteriosclerosis as a consequence of metabolic diseases or the process of aging, there is a healing and/or preventive effect as this pharmaceutical drug inhibits the migration of lymphocytes, neutrophils and monocytes into the vessel wall, thus inhibiting the progredience of arteriosclerotic plaque resulting therefrom.

The pharmaceutical drug according to the invention may also be used for the transportation of another drug. The inventive drug specifically binds a surface molecule on endothelial cells. Thus drugs linked thereto may be delivered to endothelial cells in high concentrations without any danger of them having side effects at other sites. An example that may be cited here is the use of substances inhibiting the division of cells, which, specifically brought to endothelial cells, may have an antiangiogenetic effect. This brings about a healing effect in tumor patients, as tumor growth is blocked by preventing the proliferation of endothelial cells and thus by preventing neoangiogenesis. The inventive compounds themselves may also develop an antiangiogenetic effect, as they, because of their endothelium-stabilizing effect, prevent the endothelial cells from changing into a proliferative phenotype and thus prevent the formation of new capillary blood vessels. Therefore they are themselves suitable for the treatment of all kinds of tumor diseases as well as the prevention and/or treatment of tumor metastases.

The inventive compounds of Formula (I) together with pharmaceutical adjuvants and additives, may be formulated into pharmaceutical preparations which also are a subject matter of the present invention. In order to prepare such formulations a therapeutically effective dose of the peptide or peptide derivative is mixed with pharmaceutically acceptable diluents, stabilizers, solubilizers, emulsifying aids, adjuvants or carriers and brought into a suitable therapeutic form. Such preparations for instance contain a dilution of various buffers (e.g. Tris-HCl, acetate, phosphate) of different pH and ionic strength, detergents and solubilizers (e.g. Tween 80, Polysorbat 80), antioxidants (e.g. ascorbic acid), and fillers (e.g. lactose, mannitol). These formulations may influence the biological availability and the metabolic behavior of the active agents.

The pharmaceutical preparations according to the invention may be administered orally, parenterally (intramuscularly, intraperitoneally, intravenously or subcutaneously), transdermally or in an erodible implant of a suitable biologically degradable polymer (e.g. polylactate or polyglycolate).

The effectiveness of the compounds according to this invention with respect to the prevention of RhoA activation and consequently the change in the cytoskeletal structure of the endothelial cells may for instance be demonstrated by a method comprising the steps of:

a. contacting a confluent layer of cultured endothelial cells with thrombin in the presence of at least one of the test compounds
b. lysing the endothelial cells with a lysation buffer
c. measuring the RhoA activity with a specific assay, preferentially a so-called "pull down assay".

The effectiveness in vivo may for instance be established using a model of acute pulmonitis in a rodent. The acute pulmonitis is for instance caused in mice by the intratracheal instillation of bacterial lipopolysaccharide (LPS). The effect of the active substance is measured by measuring the amount of Evans' Blue injected into the animal in pulmonary lavage or by measuring the number of extravasated leukocytes in lung lavage fluid. The inventive compounds show an effect at a dose ranging from 0.001 mg/kg body weight to 500 mg/kg body weight, preferably at a dose ranging from 0.1 mg/kg to 50 mg/kg.

A further possibility for establishing the biological effect in vivo is the reduction or complete suppression of mortality because of an infection with haemolytic viruses or bacteria. For this purpose, mice are for instance infected with a dose of Dengue viruses, wherein 50% of the animals die within a period of 5-20 days after infection. The inventive compounds bring about a reduction of this mortality at a dose ranging from 0.001 to 500 mg/kg body weight, preferably at a dose ranging from 0.1 to 50 mg/g body weight.

The following examples serve to illustrate the invention without limiting it to the examples.

General Preparation and Purification of Peptides According to the Invention

The preparation and purification of the above peptide derivatives generally takes place by way of FMOC-strategy on acid-labile resin supports using a commercially available batch peptide synthesizer as also described in the literature (e.g. "solid phase peptide synthesis—A practical approach" by E. Atherton, R. C. Sheppard, Oxford University press 1989). N-alpha-FMOC-protected derivatives, the functional side-chains of which are protected by acid-sensitive protective groups, are used as amino acid components. Unless otherwise stated, purification is carried out by means of RP-chromatography using a water/acetonitrile gradient and 0.1% TFA as ion pair reagent.

EXAMPLE 1

Gly-His-Arg-Pro-(1S, 2R)Achc-Ile-Ser-Gly-Gly
(SEQ ID NO: 3)

100 mg Tentagel (Rapp Polymere) with FMOC-Gly as the first amino acid of 0.24 mmol/g are transferred to a commercially available peptide synthesis device (PSMM(Shimadzu)), wherein the peptide sequence is constructed step-by-step according to the carbodiimide/HOBt method.

The FMOC-amino acid derivatives are pre-activated by adding a 5-fold equimolar excess of di-isopropy-carbodiimide (DIC), di-isopropy-ethylamine (DIPEA) und hydroxybenzotriazole (HOBt) and, following their transfer into the reaction vessel, mixed with the resin support for 30 minutes. Washing steps are carried out by 5 additions of 900 µl DMF and thorough mixing for 1 minute. Cleavage steps are carried out by the addition of 3×900 µl 30% piperidine in DMF and thorough mixing for 4 minutes.

Removal of the individual reaction and wash solutions is effected by forcing the solutions through the bottom frit of the reaction vessel.

The amino acid derivatives FMOC-Arg(Pbf), FMOC-Gly, FMOC-His(Trt), FMOC-Ile, FMOC-(1S,2R)-Achc, FMOC-Pro and FMOC-Ser(tBu) (NeoMPS) are employed.

When synthesis is completed the peptide resin is dried. The peptide amide is subsequently cleaved off by treatment with trifluoracetic acid/TIS/EDT/water (95:2:2:1 vol) for 2 hours at room temperature. By way of filtration, concentration of the solution and precipitation by the addition of ice-cold diethyl ether the crude product (75 mg) is obtained as a solid. The peptide is purified by RP-HPLC on Kromasil RP-18 250-20, 10 µm in 0.1% TFA with a gradient of 5 on 60% acetonitrile in 40 minutes at a flow rate of 12 ml/min and evaluation of the eluate by means of a UV detector at 215 nm. The purity of the individual fractions is determined by analyt. RP-HPLC and mass spectrometry. Following combination of the purified fractions and lyophilisation 48 mg of pure product are obtained Maldi-TOF, 909.05 m/z (m.i.).

EXAMPLE 2

Gly-His-Arg-Pro-Acdn-Ile-Ser-Gly-Gly
(SEQ ID NO: 4)

The solid phase synthesis of this compound was done according to the description in example 1; the amino acid and peptidomimetic derivatives employed in the coupling steps were: FMOC-Arg(Pbf), FMOC-Gly, FMOC-His(Trt), FMOC-Ile, FMOC-Acdn, FMOC-Pro, FMOC-Ser(tBu) (NeoMPS).

When synthesis is completed the peptide resin is dried. The peptide amide is subsequently cleaved off by treatment with trifluoracetic acid/TIS/EDT/water (95:2:2:1 vol) for 2 hours at room temperature. By way of filtration, concentration of the solution and precipitation by the addition of ice-cold diethyl ether the crude product (75 mg) is obtained as a solid.

The peptide is purified by RP-HPLC on Kromasil RP-18 250-20, 10 µm in 0.1% TFA with a gradient of 5 on 60% acetonitrile in 40 minutes at a flow rate of 12 ml/min and evaluation of the eluate by means of a UV detector at 215 nm. The purity of the individual fractions is determined by analyt. RP-HPLC and mass spectrometry. Following combination of the purified fractions and lyophilisation 48 mg of pure product are obtained. Maldi-TOF, 989.05 m/z (m.i.).

EXAMPLE 3

Gly-His-Arg-Pro-(cis-4-Acha)-Ile-Ser-Gly-Gly
(SEQ ID NO: 5)

The solid phase synthesis of this compound was done according to the description in example 1; the amino acid and peptidomimetic derivatives employed in the coupling steps were: FMOC-Arg(Pbf), FMOC-Gly, FMOC-His(Trt), FMOC-Ile, FMOC-Pro, FMOC-cis-4-Acha, FMOC-Ser(tBu) (NeoMPS).

When synthesis is completed the peptide resin is dried. The peptide amide is subsequently cleaved off by treatment with trifluoracetic acid/TIS/EDT/water (95:2:2:1 vol) for 2 hours at room temperature. By way of filtration, concentration of the solution and precipitation by the addition of ice-cold diethyl ether the crude product (75 mg) is obtained as a solid.

The peptide is purified by RP-HPLC on Kromasil RP-18 250-20, 10 μm in 0.1% TFA with a gradient of 5 on 60% acetonitrile in 40 minutes at a flow rate of 12 ml/min and evaluation of the eluate by means of a UV detector at 215 nm. The purity of the individual fractions is determined by analyt. RP-HPLC and mass spectrometry. Following combination of the purified fractions and lyophilisation 48 mg of pure product are obtained. Maldi-TOF, m/z 929.05 (m.i.).

EXAMPLE 4

```
Gly-His-Arg-Pro-Haic-Ile-Ser-Gly-Gly
(SEQ ID NO: 6)
```

The solid phase synthesis of this compound was done according to the description in example 1; the amino acid and peptidomimetic derivatives employed in the coupling steps were: FMOC-Arg(Pbf), FMOC-Gly, FMOC-His(Trt), FMOC-Ile, FMOC-Pro, FMOC-Haic, FMOC-Ser(tBu) (NeoMPS).

When synthesis is completed the peptide resin is dried. The peptide amide is subsequently cleaved off by treatment with trifluoracetic acid/TIS/EDT/water (95:2:2:1 vol) for 2 hours at room temperature. By way of filtration, concentration of the solution and precipitation by the addition of ice-cold diethyl ether the crude product (75 mg) is obtained as a solid.

The peptide is purified by RP-HPLC on Kromasil RP-18 250-20, 10 μm in 0.1% TFA with a gradient of 5 on 60% acetonitrile in 40 minutes at a flow rate of 12 ml/min and evaluation of the eluate by means of a UV detector at 215 nm. The purity of the individual fractions is determined by analyt. RP-HPLC and mass spectrometry. Following combination of the purified fractions and lyophilisation 48 mg of pure product are obtained. Maldi-TOF, 998.10 m/z (m.i.).

EXAMPLE 5

```
Gly-His-Arg-Pro-Leu-(1S, 2R)Achc-Ile-Ser-Gly-Gly
(SEQ ID NO: 7)
```

100 mg Tentagel (Rapp Polymere) with FMOC-Gly as the first amino acid of 0.24 mmol/g are transferred to a commercially available peptide synthesis device (PSMM(Shimadzu)), wherein the peptide sequence is constructed step-by-step according to the carbodiimide/HOBt method.

The FMOC-amino acid derivatives are pre-activated by adding a 5-fold equimolar excess of di-isopropy-carbodiimide (DIC), di-isopropy-ethylamine (DIPEA) und hydroxybenzotriazole (HOBt) and, following their transfer into the reaction vessel, mixed with the resin support for 30 minutes. Washing steps are carried out by 5 additions of 900 μl DMF and thorough mixing for 1 minute. Cleavage steps are carried out by the addition of 3×900 μl 30% piperidine in DMF and thorough mixing for 4 minutes.

Removal of the individual reaction and wash solutions is effected by forcing the solutions through the bottom frit of the reaction vessel.

The amino acid derivatives FMOC-Arg(Pbf), FMOC-Gly, FMOC-His(Trt), FMOC-Leu, FMOC-Ile, FMOC-(1S,2R)-Achc, FMOC-Pro and FMOC-Ser(tBu) (NeoMPS) are employed.

When synthesis is completed the peptide resin is dried. The peptide amide is subsequently cleaved off by treatment with trifluoracetic acid/TIS/EDT/water (95:2:2:1 vol) for 2 hours at room temperature. By way of filtration, concentration of the solution and precipitation by the addition of ice-cold diethyl ether the crude product (75 mg) is obtained as a solid.

The peptide is purified by RP-HPLC on Kromasil RP-18 250-20, 10 μm in 0.1% TFA with a gradient of 5 on 60% acetonitrile in 40 minutes at a flow rate of 12 ml/min and evaluation of the eluate by means of a UV detector at 215 nm. The purity of the individual fractions is determined by analyt. RP-HPLC and mass spectrometry. Following combination of the purified fractions and lyophilisation 48 mg of pure product are obtained Maldi-TOF, 1023.67 m/z (m.i.).

EXAMPLE 6

```
Gly-His-Arg-Pro-Leu-Acdn-Ile-Ser-Gly-Gly
(SEQ ID NO: 8)
```

The solid phase synthesis of this compound was done according to the description in example 1; the amino acid and peptidomimetic derivatives employed in the coupling steps were: FMOC-Arg(Pbf), FMOC-Gly, FMOC-His(Trt), FMOC-Ile, FMOC-Leu, FMOC-Acdn, FMOC-Pro, FMOC-Ser(tBu) (NeoMPS).

When synthesis is completed the peptide resin is dried. The peptide amide is subsequently cleaved off by treatment with trifluoracetic acid/TIS/EDT/water (95:2:2:1 vol) for 2 hours at room temperature. By way of filtration, concentration of the solution and precipitation by the addition of ice-cold diethyl ether the crude product (75 mg) is obtained as a solid.

The peptide is purified by RP-HPLC on Kromasil RP-18 250-20, 10 μm in 0.1% TFA with a gradient of 5 on 60% acetonitrile in 40 minutes at a flow rate of 12 ml/min and evaluation of the eluate by means of a UV detector at 215 nm. The purity of the individual fractions is determined by analyt. RP-HPLC and mass spectrometry. Following combination of the purified fractions and lyophilisation 48 mg of pure product are obtained. Maldi-TOF, 1103.67 m/z (m.i.).

EXAMPLE 7

```
Gly-His-Arg-Pro-Leu-(cis-4-Acha)-Ile-Ser-Gly-Gly
(SEQ ID NO: 9)
```

The solid phase synthesis of this compound was done according to the description in example 1; the amino acid and peptidomimetic derivatives employed in the coupling steps were: FMOC-Arg(Pbf), FMOC-Gly, FMOC-His(Trt), FMOC-Leu, FMOC-Ile, FMOC-Pro, FMOC-cis-4-Acha, FMOC-Ser(tBu) (NeoMPS).

When synthesis is completed the peptide resin is dried. The peptide amide is subsequently cleaved off by treatment with trifluoracetic acid/TIS/EDT/water (95:2:2:1 vol) for 2 hours at room temperature. By way of filtration, concentration of the solution and precipitation by the addition of ice-cold diethyl ether the crude product (75 mg) is obtained as a solid.

The peptide is purified by RP-HPLC on Kromasil RP-18 250-20, 10 μm in 0.1% TFA with a gradient of 5 on 60% acetonitrile in 40 minutes at a flow rate of 12 ml/min and evaluation of the eluate by means of a UV detector at 215 nm.

EXAMPLE 8

Gly-His-Arg-Pro-Leu-Haic-Ile-Ser-Gly-Gly
    (SEQ ID NO: 10)

The solid phase synthesis of this compound was done according to the description in example 1; the amino acid and peptidomimetic derivatives employed in the coupling steps were: FMOC-Arg(Pbf), FMOC-Gly, FMOC-His(Trt), FMOC-Ile, FMOC-Leu, FMOC-Pro, FMOC-Haic, FMOC-Ser(tBu) (NeoMPS).

When synthesis is completed the peptide resin is dried. The peptide amide is subsequently cleaved off by treatment with trifluoracetic acid/TIS/EDT/water (95:2:2:1 vol) for 2 hours at room temperature. By way of filtration, concentration of the solution and precipitation by the addition of ice-cold diethyl ether the crude product (75 mg) is obtained as a solid.

The peptide is purified by RP-HPLC on Kromasil RP-18 250-20, 10 µm in 0.1% TFA with a gradient of 5 on 60% acetonitrile in 40 minutes at a flow rate of 12 ml/min and evaluation of the eluate by means of a UV detector at 215 nm. The purity of the individual fractions is determined by analyt. RP-HPLC and mass spectrometry. Following combination of the purified fractions and lyophilisation 48 mg of pure product are obtained. Maldi-TOF, 1112.27 m/z (m.i.).

EXAMPLE 9

Gly-His-Arg-Pro-Ala-(1S, 2R)Achc-Ile-Ser-Gly-Gly
    (SEQ ID NO: 11)

100 mg Tentagel (Rapp Polymere) with FMOC-Gly as the first amino acid of 0.24 mmol/g are transferred to a commercially available peptide synthesis device (PSMM(Shimadzu)), wherein the peptide sequence is constructed step-by-step according to the carbodiimide/HOBt method.

The FMOC-amino acid derivatives are pre-activated by adding a 5-fold equimolar excess of di-isopropy-carbodiimide (DIC), di-isopropy-ethylamine (DIPEA) und hydroxybenzotriazole (HOBt) and, following their transfer into the reaction vessel, mixed with the resin support for 30 minutes. Washing steps are carried out by 5 additions of 900 µl DMF and thorough mixing for 1 minute. Cleavage steps are carried out by the addition of 3×900 µl 30% piperidine in DMF and thorough mixing for 4 minutes.

Removal of the individual reaction and wash solutions is effected by forcing the solutions through the bottom frit of the reaction vessel.

The amino acid derivatives FMOC-Arg(Pbf), FMOC-Gly, FMOC-His(Trt), FMOC-Ala, FMOC-Ile, FMOC-(1S,2R)-Achc, FMOC-Pro and FMOC-Ser(tBu) (NeoMPS) are employed.

When synthesis is completed the peptide resin is dried. The peptide amide is subsequently cleaved off by treatment with trifluoracetic acid/TIS/EDT/water (95:2:2:1 vol) for 2 hours at room temperature. By way of filtration, concentration of the solution and precipitation by the addition of ice-cold diethyl ether the crude product (75 mg) is obtained as a solid.

The peptide is purified by RP-HPLC on Kromasil RP-18 250-20, 10 µm in 0.1% TFA with a gradient of 5 on 60% acetonitrile in 40 minutes at a flow rate of 12 ml/min and evaluation of the eluate by means of a UV detector at 215 nm. The purity of the individual fractions is determined by analyt. RP-HPLC and mass spectrometry. Following combination of the purified fractions and lyophilisation 48 mg of pure product are obtained Maldi-TOF, 981.14 m/z (m.i.).

EXAMPLE 10

Gly-His-Arg-Pro-Ala-Acdn-Ile-Ser-Gly-Gly
    (SEQ ID NO: 12)

The solid phase synthesis of this compound was done according to the description in example 1; the amino acid and peptidomimetic derivatives employed in the coupling steps were: FMOC-Arg(Pbf), FMOC-Gly, FMOC-His(Trt), FMOC-Ile, FMOC-Ala, FMOC-Acdn, FMOC-Pro, FMOC-Ser(tBu) (NeoMPS).

When synthesis is completed the peptide resin is dried. The peptide amide is subsequently cleaved off by treatment with trifluoracetic acid/TIS/EDT/water (95:2:2:1 vol) for 2 hours at room temperature. By way of filtration, concentration of the solution and precipitation by the addition of ice-cold diethyl ether the crude product (75 mg) is obtained as a solid.

The peptide is purified by RP-HPLC on Kromasil RP-18 250-20, 10 µm in 0.1% TFA with a gradient of 5 on 60% acetonitrile in 40 minutes at a flow rate of 12 ml/min and evaluation of the eluate by means of a UV detector at 215 nm. The purity of the individual fractions is determined by analyt. RP-HPLC and mass spectrometry. Following combination of the purified fractions and lyophilisation 48 mg of pure product are obtained. Maldi-TOF, 1061.14 m/z (m.i.).

EXAMPLE 11

Gly-His-Arg-Pro-Ile-(cis-4-Acha)-Ile-Ser-Gly-Gly
    (SEQ ID NO: 13)

The solid phase synthesis of this compound was done according to the description in example 1; the amino acid and peptidomimetic derivatives employed in the coupling steps were: FMOC-Arg(Pbf), FMOC-Gly, FMOC-His(Trt), FMOC-Ile, FMOC-Pro, FMOC-cis-4-Acha, FMOC-Ser (tBu) (NeoMPS).

When synthesis is completed the peptide resin is dried. The peptide amide is subsequently cleaved off by treatment with trifluoracetic acid/TIS/EDT/water (95:2:2:1 vol) for 2 hours at room temperature. By way of filtration, concentration of the solution and precipitation by the addition of ice-cold diethyl ether the crude product (75 mg) is obtained as a solid.

The peptide is purified by RP-HPLC on Kromasil RP-18 250-20, 10 µm in 0.1% TFA with a gradient of 5 on 60% acetonitrile in 40 minutes at a flow rate of 12 ml/min and evaluation of the eluate by means of a UV detector at 215 nm.

The purity of the individual fractions is determined by analyt. RP-HPLC and mass spectrometry. Following combination of the purified fractions and lyophilisation 48 mg of pure product are obtained. Maldi-TOF, 1043.28 m/z (m.i.).

EXAMPLE 12

```
Gly-His-Arg-Pro-Ile-Haic-Ile-Ser-Gly-Gly
(SEQ ID NO: 14)
```

The solid phase synthesis of this compound was done according to the description in example 1; the amino acid and peptidomimetic derivatives employed in the coupling steps were: FMOC-Arg(Pbf), FMOC-Gly, FMOC-His(Trt), FMOC-Ile, FMOC-Pro, FMOC-Haic, FMOC-Ser(tBu) (NeoMPS).

When synthesis is completed the peptide resin is dried. The peptide amide is subsequently cleaved off by treatment with trifluoracetic acid/TIS/EDT/water (95:2:2:1 vol) for 2 hours at room temperature. By way of filtration, concentration of the solution and precipitation by the addition of ice-cold diethyl ether the crude product (75 mg) is obtained as a solid.

The peptide is purified by RP-HPLC on Kromasil RP-18 250-20, 10 μm in 0.1% TFA with a gradient of 5 on 60% acetonitrile in 40 minutes at a flow rate of 12 ml/min and evaluation of the eluate by means of a UV detector at 215 nm. The purity of the individual fractions is determined by analyt. RP-HPLC and mass spectrometry. Following combination of the purified fractions and lyophilisation 48 mg of pure product are obtained. Maldi-TOF, 1112.41 m/z (m.i.).

The following peptides peptidomimetics were prepared following the general procedure described in Example 1 above, using the appropriate protected building blocks:

```
Gly-His-Arg-Pro-Leu-Pro-Ile-Ser-Gly-Gly
(SEQ ID NO: 15)

Gly-His-Arg-Pro-Leu-D-Pro-Ile-Ser-Gly-Gly

Gly-His-Arg-Pro-Leu-L-hydroxyproline-Ile-Ser-Gly-
Gly (SEQ ID NO: 16)

Gly-His-Arg-Pro-Leu-D-hydroxproline-Ile-Ser-Gly-
Gly

Gly-His-Arg-Pro-Leu-L-(O-benzyl-hydroxyproline)-
Ile-Ser-Gly-Gly (SEQ ID NO: 17)

Gly-His-Arg-Pro-Leu-D-(O-benzyl-hydroxyproline)-
Ile-Ser-Gly-Gly

Gly-His-Arg-Pro-Leu-L-(O-t-butyl-hydroxyproline)-
Ile-Ser-Gly-Gly (SEQ ID NO: 18)

Gly-His-Arg-Pro-Leu-L-(O-2-naphtyl-hydroxy-
proline)-Ile-Ser-Gly-Gly (SEQ ID NO: 19)

Gly-His-Arg-Pro-Leu-L-(O-2-naphtyl-methyl-hydroxy-
proline)-Ile-Ser-Gly-Gly (SEQ ID NO: 20)

Gly-His-Arg-Pro-Leu-L-(O-phenyl-hydroxyproline)-
Ile-Ser-Gly-Gly (SEQ ID NO: 21)

Gly-His-Arg-Pro-Leu-L-4-(4-pheny-benzyl-proline)-
Ile-Ser-Gly-Gly (SEQ ID NO: 22)

Gly-His-Arg-Pro-Leu-L-(cis-3-phenyl-proline)-Ile-
Ser-Gly-Gly (SEQ ID NO: 23)

Gly-His-Arg-Pro-Leu-L-(cis-4-phenyl-proline)-Ile-
Ser-Gly-Gly (SEQ ID NO: 24)

Gly-His-Arg-Pro-Leu-L-(trans-4-phenyl-proline)-
Ile-Ser-Gly-Gly (SEQ ID NO: 25)

Gly-His-Arg-Pro-Leu-L-(cis-5-phenyl-proline)-Ile-
Ser-Gly-Gly-Gly (SEQ ID NO: 26)

Gly-His-Arg-Pro-Leu-L-(trans-5-phenyl-proline)-
Ile-Ser-Gly-Gly (SEQ ID NO: 27)

Gly-His-Arg-Pro-Leu-L-(4-benzyl-proline)-Ile-Ser-
Gly-Gly (SEQ ID NO: 28)

Gly-His-Arg-Pro-Leu-L-(4-(4-bromobenzyl)-proline)-
Ile-Ser-Gly-Gly (SEQ ID NO: 29)

Gly-His-Arg-Pro-Leu-L-(4-cyclohexyl-proline)-Ile-
Ser-Gly-Gly (SEQ ID NO: 30)

Gly-His-Arg-Pro-Leu-L-(4-fluoro-proline)-Ile-Ser-
Gly-Gly (SEQ ID NO: 31)

Gly-His-Arg-Pro-Leu-L-Tic-Ile-Ser-Gly-Gly
(SEQ ID NO: 32)

Gly-His-Arg-Pro-Leu-(SSS)-Oic-Ile-Ser-Gly-Gly
(SEQ ID NO: 33)

Gly-His-Arg-Pro-Leu-(SSS)1-aza-bicyclo[3.3.0]
bicyclooctan-carboxyl-Ile-Ser-Gly-Gly
(SEQ ID NO: 34)

Gly-His-Arg-Pro-Leu-cis-Acpc-Ile-Ser-Gly-Gly
(SEQ ID NO: 35)

Gly-His-Arg-Pro-Leu-(1R, 2R)-Acpc-Ile-Ser-Gly-Gly
(SEQ ID NO: 36)

Gly-His-Arg-Pro-Leu-(1S, 2S)-Acpc-Ile-Ser-Gly-Gly
(SEQ ID NO: 37)

Gly-His-Arg-Pro-Leu-(1-Acha)-Ile-Ser-Gly-Gly
(SEQ ID NO: 38)

Gly-His-Arg-Pro-Leu-Acpo-Ile-Ser-Gly-Gly
(SEQ ID NO: 39)

Gly-His-Arg-Pro-Leu-(1-Acbc)-Ile-Ser-Gly-Gly
(SEQ ID NO: 40)

Gly-His-Arg-Pro-Leu-Acpo-Ile-Ser-Gly-Gly
(SEQ ID NO: 41)

Gly-His-Arg-Pro-Leu-(1-Achc)-Ile-Ser-Gly-Gly
(SEQ ID NO: 42)

Gly-His-Arg-Pro-Leu-((1R, 2S)-2-Achc)-Ile-Ser-Gly-
Gly (SEQ ID NO: 43)

Gly-His-Arg-Pro-Leu-((1S, 2R)-2-Achc)-Ile-Ser-Gly-
Gly (SEQ ID NO: 44)

Gly-His-Arg-Pro-Leu-((1S, 2S)-2-Achc)-Ile-Ser-Gly-
Gly (SEQ ID NO: 45)

Gly-His-Arg-Pro-Leu-(1-Acpec)-Ile-Ser-Gly-Gly
(SEQ ID NO: 46)

Gly-His-Arg-Pro-Leu-(1-Acprc)-Ile-Ser-Gly-Gly
(SEQ ID NO: 47)

Gly-His-Arg-Pro-Leu-Aedfp-Ile-Ser-Gly-Gly
(SEQ ID NO: 48)

Gly-His-Arg-Pro-Leu-(1-Aic)-Ile-Ser-Gly-Gly
(SEQ ID NO: 49)

Gly-His-Arg-Pro-Leu-(2-Aic)-Ile-Ser-Gly-Gly
(SEQ ID NO: 50)
```

Gly-His-Arg-Pro-Leu-Ambc-Ile-Ser-Gly-Gly
(SEQ ID NO: 51)

Gly-His-Arg-Pro-Leu-Ampa-Ile-Ser-Gly-Gly
(SEQ ID NO: 52)

Gly-His-Arg-Pro-Leu-Anc-Ile-Ser-Gly-Gly
(SEQ ID NO: 53)

Gly-His-Arg-Pro-Leu-Atpc-Ile-Ser-Gly-Gly
(SEQ ID NO: 54)

Gly-His-Arg-Pro-Leu-(2-Atc)-Ile-Ser-Gly-Gly
(SEQ ID NO: 55)

Gly-His-Arg-Pro-Leu-Acbt-Ile-Ser-Gly-Gly
(SEQ ID NO: 56)

Gly-His-Arg-Pro-Leu-Acbo-Ile-Ser-Gly-Gly
(SEQ ID NO: 57)

Gly-His-Arg-Pro-Leu-(1-Acmb)-Ile-Ser-Gly-Gly
(SEQ ID NO: 58)

Gly-His-Arg-Pro-Leu-(2-Acmb)-Ile-Ser-Gly-Gly
(SEQ ID NO: 59)

Gly-His-Arg-Pro-Leu-Acmv-Ile-Ser-Gly-Gly
(SEQ ID NO: 60)

Gly-His-Arg-Pro-Leu-Acq-Ile-Ser-Gly-Gly
(SEQ ID NO: 61)

Gly-His-Arg-Pro-Leu-Accb-Ile-Ser-Gly-Gly
(SEQ ID NO: 62)

Gly-His-Arg-Pro-Leu-Acpb-Ile-Ser-Gly-Gly
(SEQ ID NO: 63)

Gly-His-Arg-Pro-Leu-PBD-Ile-Ser-Gly-Gly
(SEQ ID NO: 64)

Gly-His-Arg-Pro-Leu-ppp-Ile-Ser-Gly-Gly
(SEQ ID NO: 65)

Gly-His-Arg-Pro-Leu-Cptd-Ile-Ser-Gly-Gly
(SEQ ID NO: 66)

Gly-His-Arg-Pro-Leu-Thc-Ile-Ser-Gly-Gly
(SEQ ID NO: 67)

Gly-His-Arg-Pro-Leu-bhc-Ile-Ser-Gly-Gly
(SEQ ID NO: 68)

Gly-His-Arg-Pro-Leu-Accl-Ile-Ser-Gly-Gly
(SEQ ID NO: 69)

Gly-His-Arg-Pro-Leu-PLSP-Ile-Ser-Gly-Gly
(SEQ ID NO: 70)

Gly-His-Arg-Pro-Leu-BTD-Ile-Ser-Gly-Gly
(SEQ ID NO: 71)

Gly-His-Arg-Pro-Pro-Ile-Ser-Gly-Gly-
(SEQ ID NO: 72)

Gly-His-Arg-Pro-D-Pro-Ile-Ser-Gly-Gly

Gly-His-Arg-Pro-L-hydroxyproline-Ile-Ser-Gly-Gly
(SEQ ID NO: 73)

Gly-His-Arg-Pro-D-hydroxproline-Ile-Ser-Gly-Gly

Gly-His-Arg-Pro-L-(O-benzyl-hydroxyproline)-Ile-Ser-Gly-Gly (SEQ ID NO: 74)

Gly-His-Arg-Pro-D-(O-benzyl-hydroxyproline)-Ile-Ser-Gly-Gly

Gly-His-Arg-Pro-L-(O-t-butyl-hydroxyproline)-Ile-Ser-Gly-Gly (SEQ ID NO: 75)

Gly-His-Arg-Pro-L-(O-2-naphtyl-hydroxyproline)-Ile-Ser-Gly-Gly (SEQ ID NO: 76)

Gly-His-Arg-Pro-L-(O-2-naphtyl-methyl-hydroxyproline)-Ile-Ser-Gly-Gly (SEQ ID NO: 77)

Gly-His-Arg-Pro-L-(O-phenyl-hydroxyproline)-Ile-Ser-Gly-Gly (SEQ ID NO: 78)

Gly-His-Arg-Pro-L-4-(4-pheny-benzyl-proline)-Ile-Ser-Gly-Gly (SEQ ID NO: 79)

Gly-His-Arg-Pro-L-(cis-3-phenyl-proline)-Ile-Ser-Gly-Gly (SEQ ID NO: 80)

Gly-His-Arg-Pro-L-(cis-4-phenyl-proline)-Ile-Ser-Gly-Gly (SEQ ID NO: 81)

Gly-His-Arg-Pro-L-(trans-4-phenyl-proline)-Ile-Ser-Gly-Gly (SEQ ID NO: 82)

Gly-His-Arg-Pro-L-(cis-5-phenyl-proline)-Ile-Ser-Gly-Gly (SEQ ID NO: 83)

Gly-His-Arg-Pro-L-(trans-5-phenyl-proline)-Ile-Ser-Gly-Gly (SEQ ID NO: 84)

Gly-His-Arg-Pro-L-(4-benzyl-proline)-Ile-Ser-Gly-Gly (SEQ ID NO: 85)

Gly-His-Arg-Pro-L-(4-(4-bromobenzyl)-proline)-Ile-Ser-Gly-Gly (SEQ ID NO: 86)

Gly-His-Arg-Pro-L-(4-cyclohexyl-proline)-Ile-Ser-Gly-Gly (SEQ ID NO: 87)

Gly-His-Arg-Pro-L-(4-fluoro-proline)-Ile-Ser-Gly-Gly (SEQ ID NO: 88)

Gly-His-Arg-Pro-L-Tic-Ile-Ser-Gly-Gly
(SEQ ID NO: 89)

Gly-His-Arg-Pro-(SSS)-Oic-Ile-Ser-Gly-Gly
(SEQ ID NO: 90)

Gly-His-Arg-Pro-(SSS)1-aza-bicyclo[3.3.0]bicyclo-octan-carboxyl-Ile-Ser-Gly-Gly (SEQ ID NO: 91)

Gly-His-Arg-Pro-cis-Acpc-Ile-Ser-Gly-Gly
(SEQ ID NO: 92)

Gly-His-Arg-Pro-(1R, 2R)-Acpc-Ile-Ser-Gly-Gly
(SEQ ID NO: 93)

Gly-His-Arg-Pro-(1S, 2S)-Acpc-Ile-Ser-Gly-Gly
(SEQ ID NO: 94)

Gly-His-Arg-Pro-(1-Acha)-Ile-Ser-Gly-Gly
(SEQ ID NO: 95)

Gly-His-Arg-Pro-Acpo-Ile-Ser-Gly-Gly
(SEQ ID NO: 96)

Gly-His-Arg-Pro-(1-Acbc)-Ile-Ser-Gly-Gly
(SEQ ID NO: 97)

Gly-His-Arg-Pro-Acpo-Ile-Ser-Gly-Gly-
(SEQ ID NO: 98)

Gly-His-Arg-Pro-(1-Achc)-Ile-Ser-Gly-Gly
(SEQ ID NO: 99)

Gly-His-Arg-Pro-((1R, 2S)-2-Achc)-Ile-Ser-Gly-Gly
(SEQ ID NO: 100)

Gly-His-Arg-Pro-((1S ,2R)-2-Achc)-Ile-Ser-Gly-Gly
(SEQ ID NO: 101)

-continued

Gly-His-Arg-Pro-((1S ,2S)-2-Achc)-Ile-Ser-Gly-Gly
(SEQ ID NO: 102)

Gly-His-Arg-Pro-(1-Acpec)-Ile-Ser-Gly-Gly
(SEQ ID NO: 103)

Gly-His-Arg-Pro-(1-Acprc)-Ile-Ser-Gly-Gly
(SEQ ID NO: 104)

Gly-His-Arg-Pro-Aedfp-Ile-Ser-Gly-Gly
(SEQ ID NO: 105)

Gly-His-Arg-Pro-(1-Aic)-Ile-Ser-Gly-Gly
(SEQ ID NO: 106)

Gly-His-Arg-Pro-(2-Aic)-Ile-Ser-Gly-Gly
(SEQ ID NO: 107)

Gly-His-Arg-Pro-Ambc-Ile-Ser-Gly-Gly
(SEQ ID NO: 108)

Gly-His-Arg-Pro-Ampa-Ile-Ser-Gly-Gly
(SEQ ID NO: 109)

Gly-His-Arg-Pro-Leu-Asp-Lys-Anc-Ile-Ser-Gly-Gly
(SEQ ID NO: 110)

Gly-His-Arg-Pro-Atpc-Ile-Ser-Gly-Gly
(SEQ ID NO: 111)

Gly-His-Arg-Pro-(2-Atc)-Ile-Ser-Gly-Gly
(SEQ ID NO: 112)

Gly-His-Arg-Pro-Acbt-Ile-Ser-Gly-Gly
(SEQ ID NO: 113)

Gly-His-Arg-Pro-Acbo-Ile-Ser-Gly-Gly
(SEQ ID NO: 114)

Gly-His-Arg-Pro-(1-Acmb)-Ile-Ser-Gly-Gly
(SEQ ID NO: 115)

Gly-His-Arg-Pro-(2-Acmb)-Ile-Ser-Gly-Gly
(SEQ ID NO: 116)

Gly-His-Arg-Pro-Acmv-Ile-Ser-Gly-Gly
(SEQ ID NO: 117)

Gly-His-Arg-Pro-Acq-Ile-Ser-Gly-Gly
(SEQ ID NO: 118)

Gly-His-Arg-Pro-Accb-Ile-Ser-Gly-Gly
(SEQ ID NO: 119)

Gly-His-Arg-Pro-Acpb-Ile-Ser-Gly-Gly
(SEQ ID NO: 120)

Gly-His-Arg-Pro-PBD-Ile-Ser-Gly-Gly
(SEQ ID NO: 121)

Gly-His-Arg-Pro-Bppp-Ile-Ser-Gly-Gly
(SEQ ID NO: 122)

Gly-His-Arg-Pro-Cptd-Ile-Ser-Gly-Gly
(SEQ ID NO: 123)

Gly-His-Arg-Pro-Thc-Ile-Ser-Gly-Gly
(SEQ ID NO: 124)

Gly-His-Arg-Pro-Abhc-Ile-Ser-Gly-Gly
(SEQ ID NO: 125)

Gly-His-Arg-Pro-Accl-Ile-Ser-Gly-Gly
(SEQ ID NO: 126)

Gly-His-Arg-Pro-PLSP-Ile-Ser-Gly-Gly
(SEQ ID NO: 127)

Gly-His-Arg-Pro-BTD-Ile-Ser-Gly-Gly
(SEQ ID NO: 128)

EXAMPLE 13

Gly-His-Arg-Pro-(1S, 2R)Achc-Ile-Ser-Gly-Gly-$NH_2$
(SEQ ID NO: 129)

100 mg Tentagel-S-RAM (Rapp-Polymere) at a load of 0.24 mmol/g are transferred to a commercially available peptide synthesis device (PSMM(Shimadzu)), wherein the peptide sequence is constructed step-by-step according to the carbodiimide/HOBt method.

The FMOC-amino acid derivatives are pre-activated by adding a 5-fold equimolar excess of di-isopropy-carbodiimide (DIC), di-isopropy-ethylamine (DIPEA) und hydroxybenzotriazole (HOBt) and, following their transfer into the reaction vessel, mixed with the resin support for 30 minutes. Washing steps are carried out by 5 additions of 900 µl DMF and thorough mixing for 1 minute. Cleavage steps are carried out by the addition of 3×900 µl 30% piperidine in DMF and thorough mixing for 4 minutes.

Removal of the individual reaction and wash solutions is effected by forcing the solutions through the bottom frit of the reaction vessel.

The amino acid derivatives FMOC-Arg(Pbf), FMOC-Gly, FMOC-His(Trt), FMOC-Ile, FMOC-(1S,2R)-Achc, and FMOC-Ser(tBu) (NeoMPS) are employed.

When synthesis is completed the peptide resin is dried. The peptide amide is subsequently cleaved off by treatment with trifluoracetic acid/TIS/EDT/water (95:2:2:1 vol) for 2 hours at room temperature. By way of filtration, concentration of the solution and precipitation by the addition of ice-cold diethyl ether the crude product (75 mg) is obtained as a solid.

The peptide is purified by RP-HPLC on Kromasil RP-18 250-20, 10 µm in 0.1% TFA with a gradient of 5 on 60% acetonitrile in 40 minutes at a flow rate of 12 ml/min and evaluation of the eluate by means of a UV detector at 215 nm. The purity of the individual fractions is determined by analyt. RP-HPLC and mass spectrometry. Following combination of the purified fractions and lyophilisation 48 mg of pure product are obtained, Molecular weight by mass spectrometry: 908.08 (MALDI-TOF)

EXAMPLE 14

Gly-His-Arg-Pro-Leu-Acdn-Ile-Ser-Gly-Gly-$NH_2$
(SEQ ID NO: 130)

The solid phase synthesis of this compound was done according to the description in example 1; the amino acid and peptidomimetic derivatives employed in the coupling steps were: FMOC-Arg(Pbf), FMOC-Asp, FMOC-Gly, FMOC-His(Trt), FMOC-Ile, FMOC-Leu, FMOC-Acdn, and FMOC-Ser(tBu) (NeoMPS).

When synthesis is completed the peptide resin is dried. The peptide amide is subsequently cleaved off by treatment with trifluoracetic acid/TIS/EDT/water (95:2:2:1 vol) for 2 hours at room temperature. By way of filtration, concentration of the solution and precipitation by the addition of ice-cold diethyl ether the crude product (75 mg) is obtained as a solid.

The peptide is purified by RP-HPLC on Kromasil RP-18 250-20, 10 µm in 0.1% TFA with a gradient of 5 on 60% acetonitrile in 40 minutes at a flow rate of 12 ml/min and evaluation of the eluate by means of a UV detector at 215 nm.

The purity of the individual fractions is determined by analyt. RP-HPLC and mass spectrometry. Following combination of the purified fractions and lyophilisation 48 mg of pure product are obtained. Maldi-TOF, 998.01 m/z (m.i.).

The following peptides peptidomimetics were prepared following the general procedure described in Example 1 above, using the appropriate protected building blocks:

```
Gly-His-Arg-Pro-Pro-Ile-Ser-Gly-Gly-NH2
(SEQ ID NO: 131)

Gly-His-Arg-Pro-D-Pro-Ile-Ser-Gly-Gly-NH2

Gly-His-Arg-Pro-L-hydroxyproline-Ile-Ser-Gly-Gly-
NH2 (SEQ ID NO: 132)

Gly-His-Arg-Pro-Leu-D-hydroxproline-Ile-Ser-Gly-
Gly-NH2

Gly-His-Arg-Pro-Leu-L-(O-benzyl-hydroxyproline)-
Ile-Ser-Gly-Gly-NH2 (SEQ ID NO: 133)

Gly-His-Arg-Pro-D-(O-benzyl-hydroxyproline)-Ile-
Ser-Gly-Gly-NH2

Gly-His-Arg-Pro-Leu-L-(O-t-butyl-hydroxyproline)-
Ile-Ser-Gly-Gly-NH2 (SEQ ID NO: 134)

Gly-His-Arg-Pro-L-(O-2-naphtyl-hydroxyproline)-
Ile-Ser-Gly-Gly-NH2 (SEQ ID NO: 135)

Gly-His-Arg-Pro-L-(O-2-naphtyl-methyl-hydroxy-
proline)-Ile-Ser-Gly-Gly-NH2 (SEQ ID NO: 136)

Gly-His-Arg-Pro-Leu-L-(O-phenyl-hydroxyproline)-
Ile-Ser-Gly-Gly-NH2 (SEQ ID NO: 137)

Gly-His-Arg-Pro-4-(4-pheny-benzyl-proline)-Ile-
Ser-Gly-Gly-NH2 (SEQ ID NO: 138)

Gly-His-Arg-Pro-L-(cis-3-phenyl-proline)-Ile-Ser-
Gly-Gly-NH2 (SEQ ID NO: 139)

Gly-His-Arg-Pro-Leu-L-(cis-4-phenyl-proline)-Ile-
Ser-Gly-Gly-NH2 (SEQ ID NO: 140)

Gly-His-Arg-Pro-L-(trans-4-phenyl-proline)-Ile-
Ser-Gly-Gly-NH2 (SEQ ID NO: 141)

Gly-His-Arg-Pro-Leu-L-(cis-5-phenyl-proline)-Ile-
Ser-Gly-Gly-NH2 (SEQ ID NO: 142)

Gly-His-Arg-Pro-L-(trans-5-phenyl-proline)-Ile-
Ser-Gly-Gly-NH2 (SEQ ID NO: 143)

Gly-His-Arg-Pro-L-(4-benzyl-proline)-Ile-Ser-Gly-
Gly-NH2 (SEQ ID NO: 144)

Gly-His-Arg-Pro-L-(4-(4-bromobenzyl)-proline)-Ile-
Ser-Gly-Gly-NH2 (SEQ ID NO: 145)

Gly-His-Arg-Pro-Ala-L-(4-cyclohexyl-proline)-Ile-
Ser-Gly-Gly-NH2 (SEQ ID NO: 146)

Gly-His-Arg-Pro-Ile-L-(4-fluoro-proline)-Ile-Ser-
Gly-Gly-NH2 (SEQ ID NO: 147)

Gly-His-Arg-Pro-Leu-Asp-Lys-L-Tic-Ile-Ser-Gly-Gly-
Gly-Tyr-Arg-NH2 (SEQ ID NO: 148)

Gly-His-Arg-Pro-(SSS)-Oic-Ile-Ser-Gly-Gly-NH2
(SEQ ID NO: 149)

Gly-His-Arg-Pro-(SSS)1-aza-bicyclo[3.3.0]bicyclo-
octan-carboxyl-Ile-Ser-Gly-Gly-NH2 (SEQ ID NO: 150)

Gly-His-Arg-Pro-Ala-cis-Acpc-Ile-Ser-Gly-Gly-NH2
(SEQ ID NO: 151)

Gly-His-Arg-Pro-(1R, 2R)-Acpc-Ile-Ser-Gly-GlyNH2
(SEQ ID NO: 152)

Gly-His-Arg-Pro-Leu-(1S, 2S)-Acpc-Ile-Ser-Gly-Gly-
NH2 (SEQ ID NO: 153)

Gly-His-Arg-Pro-Ile-(1-Acha)-Ile-Ser-Gly-Gly-NH2
(SEQ ID NO: 154)

Gly-His-Arg-Pro-Acpo-Ile-Ser-Gly-Gly-NH2
(SEQ ID NO: 155)

Gly-His-Arg-Pro-(1-Acbc)-Ile-Ser-Gly-Gly-NH2
(SEQ ID NO: 156)

Gly-His-Arg-Pro-Leu-Acpo-Ile-Ser-Gly-Gly-NH2
(SEQ ID NO: 157)

Gly-His-Arg-Pro-Ala-(1-Achc)-Ile-Ser-Gly-Gly-NH2
(SEQ ID NO: 158)

Gly-His-Arg-Pro-((1R, 2S)-2-Achc)-Ile-Ser-Gly-Gly-
NH2 (SEQ ID NO: 159)

Gly-His-Arg-Pro-Val-((1S, 2R)-2-Achc)-Ile-Ser-Gly-
Gly-NH2 (SEQ ID NO: 160)

Gly-His-Arg-Pro-((1S, 2S)-2-Achc)-Ile-Ser-Gly-Gly-NH2
(SEQ ID NO: 161)

Gly-His-Arg-Pro-Leu-(1-Acpec)-Ile-Ser-Gly-Gly-NH2
(SEQ ID NO: 162)

Gly-His-Arg-Pro-(1-Acprc)-Ile-Ser-Gly-Gly-NH2
(SEQ ID NO: 163)

Gly-His-Arg-Pro-Aedfp-Ile-Ser-Gly-Gly-NH2
(SEQ ID NO: 164)

Gly-His-Arg-Pro-Val-(1-Aic)-Ile-Ser-Gly-Gly-NH2
(SEQ ID NO: 165)

Gly-His-Arg-Pro-(2-Aic)-Ile-Ser-Gly-Gly-NH2
(SEQ ID NO: 166)

Gly-His-Arg-Pro-LeuAmbc-Ile-Ser-Gly-Gly-NH2
(SEQ ID NO: 167)

Gly-His-Arg-Pro-Ampa-Ile-Ser-Gly-Gly-NH2
(SEQ ID NO: 168)

Gly-His-Arg-Pro-Ile-Anc-Ile-Ser-Gly-Gly-NH2
(SEQ ID NO: 169)

Gly-His-Arg-Pro-Atpc-Ile-Ser-Gly-Gly-NH2
(SEQ ID NO: 170)

Gly-His-Arg-Pro-Ala-(2-Atc)-Ile-Ser-Gly-Gly-NH2
(SEQ ID NO: 171)

Gly-His-Arg-Pro-Leu-Acbt-Ile-Ser-Gly-Gly-NH2
(SEQ ID NO: 172)

Gly-His-Arg-Pro-Acbo-Ile-Ser-Gly-Gly-NH2
(SEQ ID NO: 173)

Gly-His-Arg-Pro-Leu-(1-Acmb)-Ile-Ser-Gly-Gly-NH2
(SEQ ID NO: 174)

Gly-His-Arg-Pro-Leu-(2-Acmb)-Ile-Ser-Gly-Gly-NH2
(SEQ ID NO: 175)

Gly-His-Arg-Pro-Acmv-Ile-Ser-Gly-Gly-NH2
(SEQ ID NO: 176)

Gly-His-Arg-Pro-Acq-Ile-Ser-Gly-Gly-NH2
(SEQ ID NO: 177)

Gly-His-Arg-Pro-Ala-Haic-Ile-Ser-Gly-Gly-NH2
(SEQ ID NO: 178)
```

-continued

Gly-His-Arg-Pro-Accb-Ile-Ser-Gly-Gly-NH$_2$
(SEQ ID NO: 179)

Gly-His-Arg-Pro-Acpb-Ile-Ser-Gly-Gly-NH$_2$
(SEQ ID NO: 180)

Gly-His-Arg-Pro-Leu-PBD-Ile-Ser-Gly-Gly-NH$_2$
(SEQ ID NO: 181)

Gly-His-Arg-Pro-Ala-Bppp-Ile-Ser-Gly-Gly-NH$_2$
(SEQ ID NO: 182)

Gly-His-Arg-Pro-Cptd-Ile-Ser-Gly-Gly-NH$_2$
(SEQ ID NO: 183)

Gly-His-Arg-Pro-Leu-Thc-Ile-Ser-Gly-Gly-NH$_2$
(SEQ ID NO: 184)

Gly-His-Arg-Pro-Abhc-Ile-Ser-Gly-Gly-NH$_2$
(SEQ ID NO: 185)

Gly-His-Arg-Pro-Ala-Accl-Ile-Ser-Gly-Gly-NH$_2$
(SEQ ID NO: 186)

Gly-His-Arg-Pro-Leu-PLSP-Ile-Ser-Gly-Gly-NH$_2$
(SEQ ID NO: 187)

Gly-His-Arg-Pro-BTD-Ile-Ser-Gly-Gly-NH$_2$
(SEQ ID NO: 188)

EXAMPLE 15

Gly-His-Arg-Pro-(1S, 2R)Achc-Ile-Ser-Gly-Gly-Cys-(S-succinimido-PEG$_{20K}$)-amide (SEQ ID NO: 189)

The monomeric peptide is synthesized as in Example 1, Tentagel (Rapp Polymere) being used as resin support here with FMOC-Cys(Trt) as the first amino acid.

FMOC-Arg(Pbf), FMOC-Asp, FMOC-Gly, FMOC-His(Trt), FMOC-Ile, FMOC-(1S,2R)-Achc, and FMOC-Ser(tBu) (NeoMPS)

After cleavage and purification of the peptide reaction is carried out with a 2- to 8-fold molar excess of maleinimido-PEG$_{20K}$. Following recovery purification is carried out on Kromasil RP-18, and the identity of the product is confirmed by way of analytical RP-HPLC and MALDI-MS.

EXAMPLE 16

Gly-His-Arg-Pro-Acdn-Ile-Ser-Gly-Gly-Cys-(S-succinimido-PEG$_{20K}$)-amide (SEQ ID NO: 190)

The monomeric peptide is synthesized as in Example 1, Tentagel (Rapp Polymere) being used as resin support here with FMOC-Cys(Trt) as the first amino acid.

FMOC-Arg(Pbf), FMOC-Asp, FMOC-Gly, FMOC-His(Trt), FMOC-Ile, FMOC-Acdn, and FMOC-Ser(tBu) (NeoMPS)

After cleavage and purification of the peptide reaction is carried out with a 2- to 8-fold molar excess of maleinimido-PEG$_{20K}$. Following recovery purification is carried out on Kromasil RP-18, and the identity of the product is confirmed by way of analytical RP-HPLC and MALDI-MS.

Using the appropriate building blocks, the following peptide and peptidomimetic derivatives were prepared:

Gly-His-Arg-Pro-Pro-Ile-Ser-Gly-Gly-Cys-(S-succinimido-PEG$_{20K}$)-amide (SEQ ID NO: 191)

Gly-His-Arg-Pro-Leu-D-Pro-Ile-Ser-Gly-Gly-Cys-(S-succinimido-PEG$_{20K}$)-amide

Gly-His-Arg-Pro-L-hydroxyproline-Ile-Ser-Gly-Gly-Cys-(S-succinimido-PEG$_{20K}$)-amide (SEQ ID NO: 192)

Gly-His-Arg-Pro-D-hydroxproline-Ile-Ser-Gly-Gly-Cys-(S-succinimido-PEG$_{20K}$)-amide Gly-His-Arg-Pro-Leu-L-(O-benzyl-hydroxyproline)-Ile-Ser-Gly-Gly-Cys-(S-succinimido-PEG$_{20K}$)-amide (SEQ ID NO: 193)

Gly-His-Arg-Pro-D-(O-benzyl-hydroxyproline)-Ile-Ser-Gly-Gly-Cys-(S-succinimido-PEG$_{20K}$)-amide Gly-His-Arg-Pro-Leu-L-(O-t-butyl-hydroxyproline)-Ile-Ser-Gly-Gly-Cys-(S-succinimido-PEG$_{20K}$)-amide (SEQ ID NO: 194)

Gly-His-Arg-Pro-L-(O-2-naphtyl-hydroxyproline)-Ile-Ser-Gly-Gly-Cys-(S-succinimido-PEG$_{20K}$)-amide (SEQ ID NO: 195)

Gly-His-Arg-Pro-Ala-L-(O-2-naphtyl-methyl-hydroxyproline)-Ile-Ser-Gly-Gly-Cys-(S-succinimido-PEG$_{20K}$)-amide (SEQ ID NO: 196)

Gly-His-Arg-Pro-L-(O-phenyl-hydroxyproline)-Ile-Ser-Gly-Gly-Cys-(S-succinimido-PEG$_{20K}$)-amide (SEQ ID NO: 197)

Gly-His-Arg-Pro-L-4-(4-pheny-benzyl-proline)-Ile-Ser-Gly-Gly-Cys-(S-succinimido-PEG$_{20K}$)-amide (SEQ ID NO: 198)

Gly-His-Arg-Pro-Ala-L-(cis-3-phenyl-proline)-Ile-Ser-Gly-Gly-Cys-(S-succinimido-PEG$_{20K}$)-amide (SEQ ID NO: 199)

Gly-His-Arg-Pro-L-(cis-4-phenyl-proline)-Ile-Ser-Gly-Gly-Cys-(S-succinimido-PEG$_{20K}$)-amide (SEQ ID NO: 200)

Gly-His-Arg-Pro-Ala-L-(trans-4-phenyl-proline)-Ile-Ser-Gly-Gly-Cys-(S-succinimido-PEG$_{20K}$)-amide (SEQ ID NO: 201)

Gly-His-Arg-Pro-L-(cis-5-phenyl-proline)-Ile-Ser-Gly-Gly-Cys-(S-succinimido-PEG$_{20K}$)-amide (SEQ ID NO: 202)

Gly-His-Arg-Pro-L-(trans-5-phenyl-proline)-Ile-Ser-Gly-Gly-Cys-(S-succinimido-PEG$_{20K}$)-amide (SEQ ID NO: 203)

Gly-His-Arg-Pro-L-(4-benzyl-proline)-Ile-Ser-Gly-Gly-Cys-(S-succinimido-PEG$_{20K}$)-amide (SEQ ID NO: 204)

Gly-His-Arg-Pro-Leu-L-(4-(4-bromobenzyl)-proline)-Ile-Ser-Gly-Gly-Cys-(S-succinimido-PEG$_{20K}$)-amide (SEQ ID NO: 205)

Gly-His-Arg-Pro-L-(4-cyclohexyl-proline)-Ile-Ser-Gly-Gly-Cys-(S-succinimido-PEG$_{20K}$)-amide (SEQ ID NO: 206)

Gly-His-Arg-Pro-L-(4-fluoro-proline)-Ile-Ser-Gly-Gly-Cys-(S-succinimido-PEG$_{20K}$)-amide (SEQ ID NO: 207)

Gly-His-Arg-Pro-Ala-L-Tic-Ile-Ser-Gly-Gly-Cys-(S-succinimido-PEG$_{20K}$)-amide (SEQ ID NO: 208)

-continued

Gly-His-Arg-Pro-(SSS)-Oic-Ile-Ser-Gly-Gly-Cys-(S-succinimido-PEG$_{20K}$)-amide (SEQ ID NO: 209)

Gly-His-Arg-Pro-(SSS)1-aza-bicyclo[3.3.0]bicyclo-octan-carboxyl-Ile-Ser-Gly-Cys-(S-succinimido-PEG$_{20K}$)-amide (SEQ ID NO: 210)

Gly-His-Arg-Pro-Ile-cis-Acpc-Ile-Ser-Gly-Gly-Cys-(S-succinimido-PEG$_{20K}$)-amide (SEQ ID NO: 211)

Gly-His-Arg-Pro-(1R, 2R)-Acpc-Ile-Ser-Gly-Gly-Cys-(S-succlnlmldo-PEG$_{20K}$)-amide (SEQ ID NO: 212)

Gly-His-Arg-Pro-(1S, 2S)-Acpc-Ile-Ser-Gly-Gly-Cys-(S-succlnlmldo-PEG$_{20K}$)-amide (SEQ ID NO: 213)

Gly-His-Arg-Pro-Leu-(1-Acha)-Ile-Ser-Gly-Gly-Cys-(S-succinimido-PEG$_{20K}$)-amide (SEQ ID NO: 214)

Gly-His-Arg-Pro-Acpo-Ile-Ser-Gly-Gly-Cys-(S-succinimido-PEG$_{20K}$)-amide (SEQ ID NO: 215)

Gly-His-Arg-Pro-Leu-(1-Acbc)-Ile-Ser-Gly-Gly-Cys-(S-succinimido-PEG$_{20K}$)-amide (SEQ ID NO: 216)

Gly-His-Arg-Pro-Acpo-Ile-Ser-Gly-Gly-Cys-(S-succinimido-PEG$_{20K}$)-amide (SEQ ID NO: 217)

Gly-His-Arg-Pro-Ala-(1-Achc)-Ile-Ser-Gly-Gly-Cys-(S-succinimido-PEG$_{20K}$)-amide (SEQ ID NO: 218)

Gly-His-Arg-Pro-((1R, 2S)-2-Achc)-Ile-Ser-Gly-Gly-Cys-(S-succinimido-PEG$_{20K}$)-amide (SEQ ID NO: 219)

Gly-His-Arg-Pro-Leu-((1S, 2R)-2-Achc)-Ile-Ser-Gly-Gly-Cys-(S-succinimido-PEG$_{20K}$)-amide (SEQ ID NO: 220)

Gly-His-Arg-Pro-Ala-((1S, 2S)-2-Achc)-Ile-Ser-Gly-Gly-Cys-(S-succinimido-PEG$_{20K}$)-amide (SEQ ID NO: 221)

Gly-His-Arg-Pro-(1-Acpec)-Ile-Ser-Gly-Gly-Cys-(S-succinimido-PEG$_{20K}$)-amide (SEQ ID NO: 222)

Gly-His-Arg-Pro-(1-Acprc)-Ile-Ser-Gly-Gly-Cys-(S-succinimido-PEG$_{20K}$)-amide (SEQ ID NO: 223)

Gly-His-Arg-Pro-Leu-Aedfp-Ile-Ser-Gly-Gly-Cys-(S-succinimido-PEG$_{20K}$)-amide (SEQ ID NO: 224)

Gly-His-Arg-Pro-Leu-(1-Aic)-Ile-Ser-Gly-Gly-Cys-(S-succinimido-PEG$_{20K}$)-amide (SEQ ID NO: 225)

Gly-His-Arg-Pro-Ala-(2-Aic)-Ile-Ser-Gly-Gly-Cys-(S-succinimido-PEG$_{20K}$)-amide (SEQ ID NO: 226)

Gly-His-Arg-Pro-Ambc-Ile-Ser-Gly-Gly-Cys-(S-succinimido-PEG$_{20K}$)-amide (SEQ ID NO: 227)

Gly-His-Arg-Pro-Leu-Ampa-Ile-Ser-Gly-Gly-Cys-(S-succinimido-PEG$_{20K}$)-amide (SEQ ID NO: 228)

Gly-His-Arg-Pro-Anc-Ile-Ser-Gly-Gly-Cys-(S-succinimido-PEG$_{20K}$)-amide (SEQ ID NO: 229)

Gly-His-Arg-Pro-Leu-Atpc-Ile-Ser-Gly-Gly-Cys-(S-succinimido-PEG$_{20K}$)-amide (SEQ ID NO: 230)

Gly-His-Arg-Pro-Ile-(2-Atc)-Ile-Ser-Gly-Gly-Cys-(S-succinimido-PEG$_{20K}$)-amide (SEQ ID NO: 231)

Gly-His-Arg-Pro-Acbt-Ile-Ser-Gly-Gly-Cys-(S-succinimido-PEG$_{20K}$)-amide (SEQ ID NO: 232)

Gly-His-Arg-Pro-Acbo-Ile-Ser-Gly-Gly-Cys-(S-succinimido-PEG$_{20K}$)-amide (SEQ ID NO: 233)

Gly-His-Arg-Pro-Ala-(1-Acmb)-Ile-Ser-Gly-Gly-Cys-(S-succinimido-PEG$_{20K}$)-amide (SEQ ID NO: 234)

-continued

Gly-His-Arg-Pro-Lys-(2-Acmb)-Ile-Ser-Gly-Gly-Cys-(S-succinimido-PEG$_{20K}$)-amide (SEQ ID NO: 235)

Gly-His-Arg-Pro-Leu-Acmv-Ile-Ser-Gly-Gly-Cys-(S-succinimido-PEG$_{20K}$)-amide (SEQ ID NO: 236)

Gly-His-Arg-Pro-Acq-Ile-Ser-Gly-Gly-Cys-(S-succinimido-PEG$_{20K}$)-amide (SEQ ID NO: 237)

Gly-His-Arg-Pro-Leu-Haic-Ile-Ser-Gly-Gly-Cys-(S-succinimido-PEG$_{20K}$)-amide (SEQ ID NO: 238)

Gly-His-Arg-Pro-Accb-Ile-Ser-Gly-Gly-Cys-(S-succinimido-PEG$_{20K}$)-amide (SEQ ID NO: 239)

Gly-His-Arg-Pro-Ala-Acpb-Ile-Ser-Gly-Gly-Cys-(S-succinimido-PEG$_{20K}$)-amide (SEQ ID NO: 240)

Gly-His-Arg-Pro-Leu-PBD-Ile-Ser-Gly-Gly-Cys-(S-succinimido-PEG$_{20K}$)-amide (SEQ ID NO: 241)

Gly-His-Arg-Pro-Bppp-Ile-Ser-Gly-Gly-Cys-(S-succinimido-PEG$_{20K}$)-amide (SEQ ID NO: 242)

Gly-His-Arg-Pro-Leu-Cptd-Ile-Ser-Gly-Gly-Cys-(S-succinimido-PEG$_{20K}$)-amide (SEQ ID NO: 243)

Gly-His-Arg-Pro-Thc-Ile-Ser-Gly-Gly-Cys-(S-succinimido-PEG$_{20K}$)-amide (SEQ ID NO: 244)

Gly-His-Arg-Pro-Leu-Abhc-Ile-Ser-Gly-Gly-Cys-(S-succinimido-PEG$_{20K}$)-amide (SEQ ID NO: 245)

Gly-His-Arg-Pro-Accl-Ile-Ser-Gly-Gly-Cys-(S-succinimido-PEG$_{20K}$)-amide (SEQ ID NO: 246)

Gly-His-Arg-Pro-Ala-PLSP-Ile-Ser-Gly-Gly-Cys-(S-succinimido-PEG$_{20K}$)-amide (SEQ ID NO: 247)

Gly-His-Arg-Pro-Leu-BTD-Ile-Ser-Gly-Gly-Cys-(S-succinimido-PEG$_{20K}$)-amide (SEQ ID NO: 248)

Gly-His-Arg-Pro-(1S, 2R)Achc-Ile-Ser-Gly-Gly-Cys-(S-succinimido-PEG$_{30K}$)-amide (SEQ ID NO: 249)

Gly-His-Arg-Pro-Leu-(1S, 2R)Achc-Ile-Ser-Gly-Gly-Cys-(S-succinimido-PEG$_{40K}$)-amide (SEQ ID NO: 250)

Gly-His-Arg-Pro-Acdn-Ile-Ser-Gly-Gly-Cys-(S-succinimido-PEG$_{30K}$)-amide (SEQ ID NO: 251)

Gly-His-Arg-Pro-Acdn-Ile-Ser-Gly-Gly-Cys-(S-succinimido-PEG$_{40K}$)-amide (SEQ ID NO: 252)

EXAMPLE 17

The biological effect of the compounds was established in a model thrombin induced RhoA activation in human umbilical vein endothelial cell (HUVEC) culture.

HUVEC are grown to confluence under standard conditions. Before induction of Rho activity HUVEC were starved for 4 h by using IMDM (Gibco) without growth factor and serum supplements. After the starvation period 5 U/ml Thrombin (Calbiochem) or 5 U thrombin plus 50 µg/ml of test compound are added to the starvation medium for 1, 5 and 10 min. Active RhoA was isolated using Rho Assay Reagent from Upstate according to manufactures instructions. Isolates were separated on a 15% polyacrylamide gel and blotted on Nitrocellulose-Membrane (Bio-Rad). RhoA was detected by using Anti-Rho (-A, -B, -C), clone55 from Upstate (1:500).

Relative RhoA stimulation compared to unstimulated control

| | |
|---|---|
| Control peptide 1 min | 1 |
| Control peptide 5 min | 1 |
| Control peptide 10 min | 1 |
| thrombin 5 min | 6.2 |
| thrombin + compound example 1 (10 min) | 2.2 |

The invention claimed is:

1. A compound of the general formula II $$H_2N-GHRPX_1-\beta-X_4X_5GGX_8X_9X_{10}-X_{11} \text{ (SEQ ID NO: 2)}$$

(II), or a physiologically acceptable salt thereof, wherein $X_1$ denotes L, I, A or is absent, $X_4$ denotes L, I, S, M or A, and $X_5$ denotes A, G, S, or L, or $X_4 X_5$ jointly denote a spacer of a length similar to 2 amino acids in chain length, $X_8$ denotes a genetically coded amino acid or is absent, $X_9$ denotes a genetically coded amino acid or is absent, $X_{10}$ denotes a genetically coded amino acid or is absent, $X_{11}$ denotes $OR_1$, wherein $R_1$ is hydrogen or $(C_1-C_{10})$alkyl, $NR_2R_3$ with $R_2$ and $R_3$ being identical or different and denoting hydrogen, $(C_1-C_{10})$alkyl or W-PEG$_{5-60K}$, wherein PEG is attached via a spacer W to the N-atom of $NR_2R_3$, or Y-Z-PEG$_{5-60K}$, wherein Y denotes a genetically coded amino acid selected from the group S, C, K or R, or is absent, and wherein Z denotes a spacer, via which polyethylene glycol (PEG) can be attached, and β denotes a genetically coded amino acid, a non-naturally occurring amino acid, or a peptidomimetic element, which induces a bend or turn in the peptide backbone of general formula II.

2. The compound of claim 1, wherein β is selected from the following:

L-proline, D-L-proline, D-proline, L-hydroxyproline, D-hydroxyproline, L-(O -benzyl)-hydroxyproline, D-(O-benzyl)-hydroxyproline, L-(O-tert.butyl)-hydroxyproline, 4-(O-2-naphtyl)-hydroxyproline, 4-(O-2-naphtyl-methyl)-hydroxyproline, 4-(O-phenyl)-hydroxyproline, 4-(4-phenyl-benzyl)-proline, cis-3-phenyl-proline, cis-4-phenyl-proline, trans-4-phenyl-proline, cis-5-phenyl-proline, trans-5-phenyl-proline, 4-benzyl-proline, 4-bromobenzyl-proline, 4-cyclohexyl-proline, 4-fluor-proline, L-tetrahydroisoquinoline-2-carboxylic acid (L-Tic), a diastereomer of octahydro-indole-2-carboxylic acid (Oic), a diastereomer of 1-aza-bicyclo[3,3,0]octane-2-carboxylic acid,

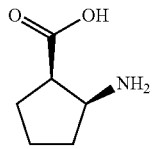

cis-2-aminocyclopentane carboxylic acid (cis-Acpc)

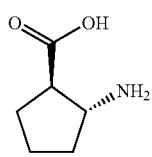

(1R,2R)-(2-aminocyclopentane carboxylic acid ((1R,2R)-Acpc)

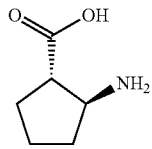

(1S,2S)-(2-aminocyclopentane carboxylic acid ((1S,2S)-Acpc)

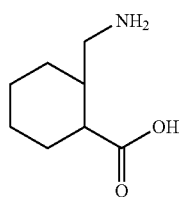

1-aminomethyl-cyclohexane acetic acid (1-Achc)

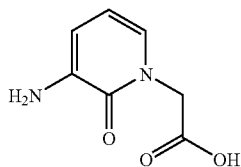

3-amino-1-carboxymethyl-pyridin-2-one (Acpo)

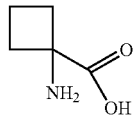

1-amino-cyclobutane-carboxylic acid (1-Acbc)

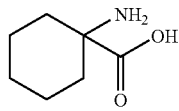

1-amino-cyclohexane-carboxylic acid (1-Achc)

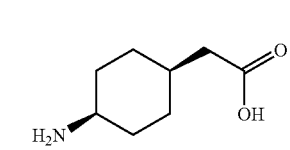

cis-4-amino-cyclohexane-acetic acid (4-Acha)

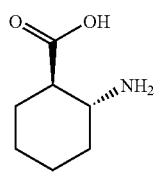

(1R,2R)-2-aminocyclohexane carboxylic acid ((1R,2R)-Achc)

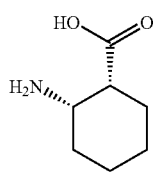

(1R,2S)-2-aminocyclohexane carboxylic acid ((1R,2S)-Achc)

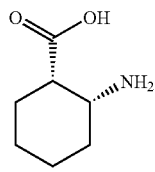

(1S,2R)-2-aminocyclohexane carboxylic acid ((1S,2R)-Achc)

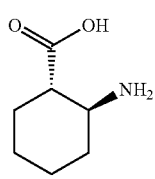

(1S,2S)-2-aminocyclohexane carboxylic acid ((1S,2S)-Achc)

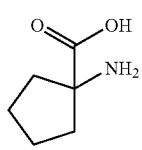

1-amino-cyclopentane carboxylic acid (1-Acpec)

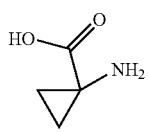

1-amino-cyclopropane carboxylic acid (1-Acprc)

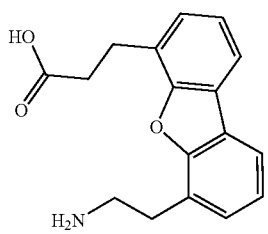

4-(2-aminoethyl)-6-dibenzofuranpropionic acid (Aedfp)

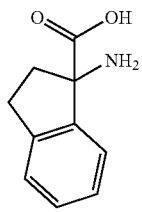

(R,S)-1-aminoindane-1-carboxylic acid (1-Aic)

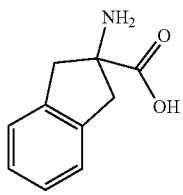

2-aminoindane-2-carboxylic acid (2-Aic)

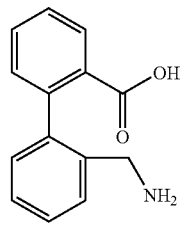

2'-(aminomethyl)-biphenyl-2-carboxylic acid (Ambc)

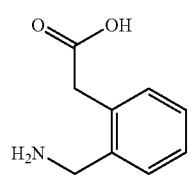

2-aminomethyl-phenylacetic acid (Ampa)

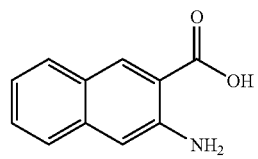

3-amino-2-naphthoic acid (Anc)

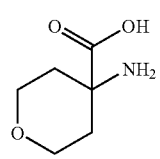

4-amino-tetrahydropyran-4-carboxylic acid (Atpc)

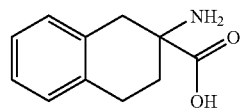

(R,S)-2-aminotetraline-2-carboxylic acid (2-Atc)

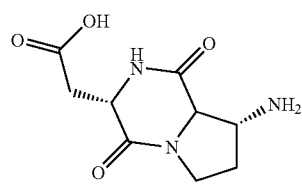

(2S,6S,9S)-6-amino-2-carboxymethyl-3,8-diazabicyclo-[4,3,0]-nonane-1,4-dione (Acdn)

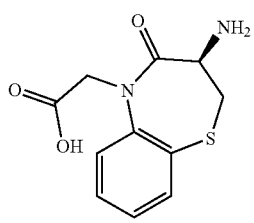

(R)-3-amino-5-carboxymethyl-2,3-dihydro-1,5-benzothiazepin-4(5H)-one (Acbt)

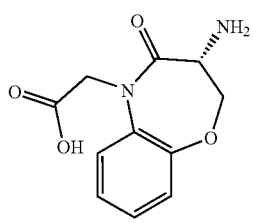

(S)-3-amino-5-carboxymethyl-2,3-dihydro-1,5-benzothiazepin-4(5H)-one (Acbt)

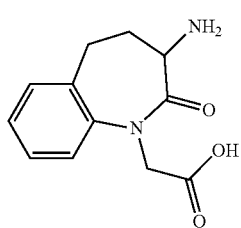

(R,S)-3-amino-1-carboxymethyl-2,3,4,5-tetrahydro-1H-[1]-benzazepin-2-one (1-Acmb)

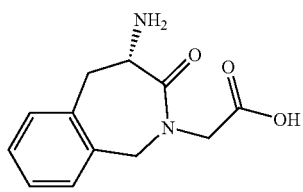

(S)-4-amino-2-carboxymethyl-1,3,4,5-tetrahydro-2H-[2]-benzazepin-3-one (2-Acmb)

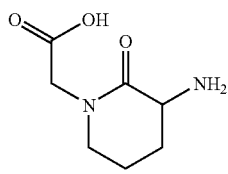

(R,S)-3-amino-1-carboxymethyl-valerolactame (Acmv)

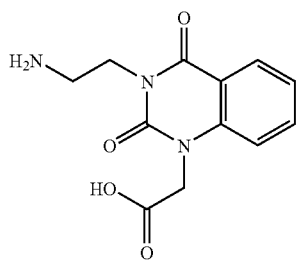

3-(2-aminoethyl)-1-carboxymethyl-quinazoline-2,4-dione (Acq)

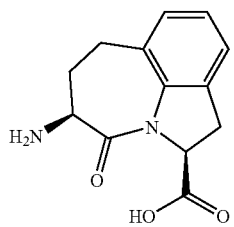

(2S,5S)-5-amino-1,2,4,5,6,7-hexahydro-azepino [3,2,1-hi]-indole-4-one-2-carboxylic acid (Haic)

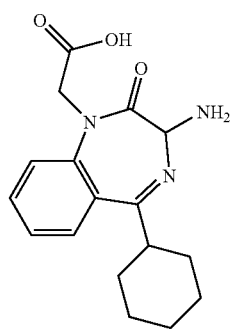

(R,S)-3-amino-N-1-carboxymethyl-2-oxo-5-cyclohexyl-1,4-benzodiazepine (Accb)

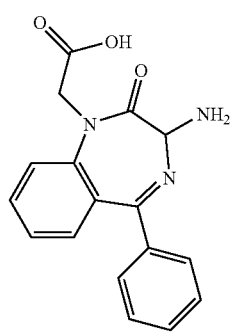

(R,S)-3-amino-N-1-carboxymethyl-2-oxo-5-phenyl-1,4-benzodiazepine (Acpb)

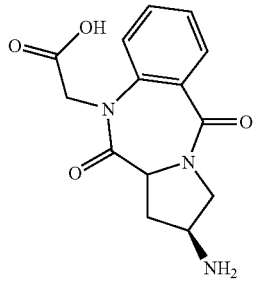

(2S,11aS)-2-amino-10-carboxymethyl-1,2,3,11 a-tetrahydro-10OH-pyrrolo[2,1-c][1,4]-benzodiazepine-5,11-dione (PBD)

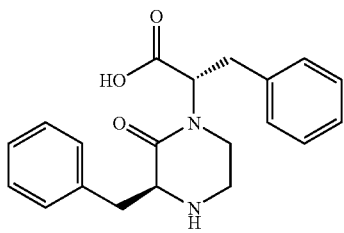

(2S,3'S)-2-(4'-(3'-benzyl-2'-oxo-piperazin-1-yl))-3-phenyl-propionic acid (Bppp)

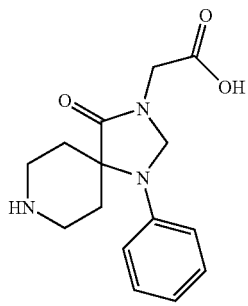

3-carboxymethyl-1-phenyl-1,3,8-triazaspiro[4.5]decan-4-one (Cptd)

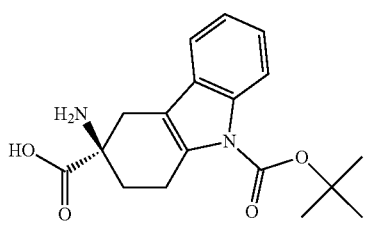

(R,S)-3-amino-9-Boc-1,2,3,4-tetrahydro-carbazole-3-carboxylic acid (Thc)

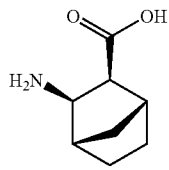

3-exo-amino-bicyclo[2.2.1]heptane-2-exo-carboxylic acid (Abhc)

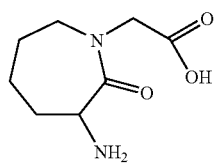

(3S)-3-amino-1-carboxymethyl-caprolactam (Accl)

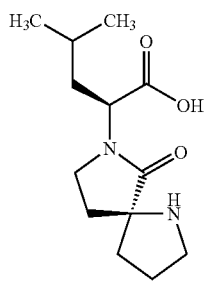

(S,S)-(ProLeu)spirolactame (PLSP) and

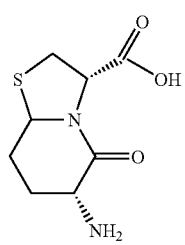

2-oxo-3-amino-7-thia-1-azabicyclo[4.3.0]nonane-9-carcoxylich acid (BTD).

3. The compound of claim 1, wherein:
$X_4$ denotes L, I, S, M or A, and
$X_5$ denotes A, G, S, or L.

4. The compound of claim 1, wherein:
$X_4$ denotes I, and
$X_5$ denotes S.

5. The compound of claim 1, wherein:
$X_1$ is absent.

6. The compound of claim 1, wherein:
$X_8$ is absent,
$X_9$ is absent, and
$X_{10}$ is absent.

7. The compound of claim 1, wherein:
β is:

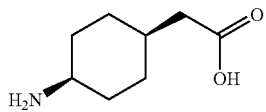

cis-4-amino-cyclohexane-acetic acid (4-Acha).

8. The compound of claim 1, wherein:
$X_1$ is absent.
$X_4$ denotes I,
$X_5$ denotes S,
$X_8$ is absent,
$X_9$ is absent,
$X_{10}$ is absent.
β is

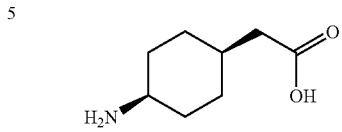

cis-4-amino-cyclohexane-acetic acid (4-Acha), and
$X_{11}$ denotes $OR_1$ wherein $R_1$ is hydrogen.

9. A pharmaceutical composition comprising the compound of claim 1.

10. A pharmaceutical composition comprising the compound of claim 8.

* * * * *

SEQUENCE LISTING

```
<160> NUMBER OF SEQ ID NOS: 253

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(13)
<223> OTHER INFORMATION: Any amino acid
<220> FEATURE:
<221> NAME/KEY: MOD_RES
<222> LOCATION: (14)..(14)
<223> OTHER INFORMATION: Any amino acid or absent
<220> FEATURE:
<223> OTHER INFORMATION: see specification as filed for detailed
      description of substitutions and preferred embodiments

<400> SEQUENCE: 1

Gly His Arg Pro Xaa Xaa Xaa Xaa Xaa Xaa Xaa Xaa Xaa Xaa
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Leu, Ile or Ala
<220> FEATURE:
<221> NAME/KEY: MOD_RES
<222> LOCATION: (6)..(6)
<223> OTHER INFORMATION: Any amino acid
<220> FEATURE:
<221> NAME/KEY: MOD_RES
<222> LOCATION: (7)..(7)
<223> OTHER INFORMATION: Leu, Ile, Ser, Met or Ala
<220> FEATURE:
<221> NAME/KEY: MOD_RES
<222> LOCATION: (8)..(8)
<223> OTHER INFORMATION: Ala, Gly, Ser or Leu
<220> FEATURE:
<221> NAME/KEY: MOD_RES
<222> LOCATION: (11)..(11)
<223> OTHER INFORMATION: Gly, Ala or Leu
<220> FEATURE:
<221> NAME/KEY: MOD_RES
<222> LOCATION: (12)..(12)
<223> OTHER INFORMATION: Tyr, Phe or His
<220> FEATURE:
<221> NAME/KEY: MOD_RES
<222> LOCATION: (13)..(13)
<223> OTHER INFORMATION: Arg or Lys
<220> FEATURE:
<221> NAME/KEY: MOD_RES
<222> LOCATION: (14)..(14)
<223> OTHER INFORMATION: Any amino acid or absent
<220> FEATURE:
```

<223> OTHER INFORMATION: see specification as filed for detailed
      description of substitutions and preferred embodiments

<400> SEQUENCE: 2

Gly His Arg Pro Xaa Xaa Xaa Xaa Gly Gly Xaa Xaa Xaa Xaa
1               5                   10

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: (1S,2R)Achc

<400> SEQUENCE: 3

Gly His Arg Pro Xaa Ile Ser Gly Gly
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Acdn

<400> SEQUENCE: 4

Gly His Arg Pro Xaa Ile Ser Gly Gly
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: cis-4-Acha

<400> SEQUENCE: 5

Gly His Arg Pro Xaa Ile Ser Gly Gly
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Haic

<400> SEQUENCE: 6

Gly His Arg Pro Xaa Ile Ser Gly Gly
1               5

```
<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: (1S,2R)Achc

<400> SEQUENCE: 7

Gly His Arg Pro Leu Xaa Ile Ser Gly Gly
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Acdn

<400> SEQUENCE: 8

Gly His Arg Pro Leu Xaa Ile Ser Gly Gly
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: cis-4-Acha

<400> SEQUENCE: 9

Gly His Arg Pro Leu Xaa Ile Ser Gly Gly
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Haic

<400> SEQUENCE: 10

Gly His Arg Pro Leu Xaa Ile Ser Gly Gly
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (6)..(6)
<223> OTHER INFORMATION: (1S,2R)Achc

<400> SEQUENCE: 11

Gly His Arg Pro Ala Xaa Ile Ser Gly Gly
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Acdn

<400> SEQUENCE: 12

Gly His Arg Pro Ala Xaa Ile Ser Gly Gly
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: cis-4-Acha

<400> SEQUENCE: 13

Gly His Arg Pro Ile Xaa Ile Ser Gly Gly
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Haic

<400> SEQUENCE: 14

Gly His Arg Pro Ile Xaa Ile Ser Gly Gly
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly His Arg Pro Leu Pro Ile Ser Gly Gly
1               5                   10

<210> SEQ ID NO 16
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: hydroxyproline

<400> SEQUENCE: 16

Gly His Arg Pro Leu Xaa Ile Ser Gly Gly
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: O-benzyl-hydroxyproline

<400> SEQUENCE: 17

Gly His Arg Pro Leu Xaa Ile Ser Gly Gly
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: O-t-butyl-hydroxyproline

<400> SEQUENCE: 18

Gly His Arg Pro Leu Xaa Ile Ser Gly Gly
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: O-2-naphtyl-hydroxyproline

<400> SEQUENCE: 19

Gly His Arg Pro Leu Xaa Ile Ser Gly Gly
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

-continued

```
<222> LOCATION: (6)..(6)
<223> OTHER INFORMATION: O-2-naphtyl-methyl-hydroxyproline

<400> SEQUENCE: 20

Gly His Arg Pro Leu Xaa Ile Ser Gly Gly
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: O-phenyl-hydroxyproline

<400> SEQUENCE: 21

Gly His Arg Pro Leu Xaa Ile Ser Gly Gly
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 4-(4-phenyl-benzyl-proline)

<400> SEQUENCE: 22

Gly His Arg Pro Leu Xaa Ile Ser Gly Gly
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: cis-3-phenyl-proline

<400> SEQUENCE: 23

Gly His Arg Pro Leu Xaa Ile Ser Gly Gly
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: cis-4-phenyl-proline

<400> SEQUENCE: 24

Gly His Arg Pro Leu Xaa Ile Ser Gly Gly
1               5                   10
```

```
<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: trans-4-phenyl-proline

<400> SEQUENCE: 25

Gly His Arg Pro Leu Xaa Ile Ser Gly Gly
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: cis-5-phenyl-proline

<400> SEQUENCE: 26

Gly His Arg Pro Leu Xaa Ile Ser Gly Gly Gly
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: trans-5-phenyl-proline

<400> SEQUENCE: 27

Gly His Arg Pro Leu Xaa Ile Ser Gly Gly
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 4-benzyl-proline

<400> SEQUENCE: 28

Gly His Arg Pro Leu Xaa Ile Ser Gly Gly
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (6)..(6)
<223> OTHER INFORMATION: 4-(4-bromobenzyl-proline)

<400> SEQUENCE: 29

Gly His Arg Pro Leu Xaa Ile Ser Gly Gly
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 4-cyclohexyl-proline

<400> SEQUENCE: 30

Gly His Arg Pro Leu Xaa Ile Ser Gly Gly
1               5                   10

<210> SEQ ID NO 31
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 4-fluoro-proline

<400> SEQUENCE: 31

Gly His Arg Pro Leu Xaa Ile Ser Gly Gly
1               5                   10

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Tic

<400> SEQUENCE: 32

Gly His Arg Pro Leu Xaa Ile Ser Gly Gly
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: SSS
<220> FEATURE:
<221> NAME/KEY: MOD_RES
<222> LOCATION: (7)..(7)
<223> OTHER INFORMATION: Oic
```

```
<400> SEQUENCE: 33

Gly His Arg Pro Leu Xaa Xaa Ile Ser Gly Gly
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: SSS
<220> FEATURE:
<221> NAME/KEY: MOD_RES
<222> LOCATION: (7)..(7)
<223> OTHER INFORMATION: 1-aza-bicyclo[3.3.0]bicyclooctan-carboxyl

<400> SEQUENCE: 34

Gly His Arg Pro Leu Xaa Xaa Ile Ser Gly Gly
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: cis-Acpc

<400> SEQUENCE: 35

Gly His Arg Pro Leu Xaa Ile Ser Gly Gly
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: (1R,2R)-Acpc

<400> SEQUENCE: 36

Gly His Arg Pro Leu Xaa Ile Ser Gly Gly
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: (1S,2S)-Acpc

<400> SEQUENCE: 37

Gly His Arg Pro Leu Xaa Ile Ser Gly Gly
```

-continued

```
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 1-Achc

<400> SEQUENCE: 38

Gly His Arg Pro Leu Xaa Ile Ser Gly Gly
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Acpo

<400> SEQUENCE: 39

Gly His Arg Pro Leu Xaa Ile Ser Gly Gly
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 1-Acbc

<400> SEQUENCE: 40

Gly His Arg Pro Leu Xaa Ile Ser Gly Gly
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Acpo

<400> SEQUENCE: 41

Gly His Arg Pro Leu Xaa Ile Ser Gly Gly
1               5                   10

<210> SEQ ID NO 42
<211> LENGTH: 10
<212> TYPE: PRT
<213> ORGANISM: Artificial Sequence
<220> FEATURE:
```

-continued

<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 1-Achc

<400> SEQUENCE: 42

Gly His Arg Pro Leu Xaa Ile Ser Gly Gly
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: (1R,2S)-2-Achc

<400> SEQUENCE: 43

Gly His Arg Pro Leu Xaa Ile Ser Gly Gly
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: (1S,2R)-2-Achc

<400> SEQUENCE: 44

Gly His Arg Pro Leu Xaa Ile Ser Gly Gly
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: (1S,2S)-2-Achc

<400> SEQUENCE: 45

Gly His Arg Pro Leu Xaa Ile Ser Gly Gly
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 1-Acpec

<400> SEQUENCE: 46

Gly His Arg Pro Leu Xaa Ile Ser Gly Gly
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 1-Acprc

<400> SEQUENCE: 47

Gly His Arg Pro Leu Xaa Ile Ser Gly Gly
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Aedfp

<400> SEQUENCE: 48

Gly His Arg Pro Leu Xaa Ile Ser Gly Gly
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 1-Aic

<400> SEQUENCE: 49

Gly His Arg Pro Leu Xaa Ile Ser Gly Gly
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 2-Aic

<400> SEQUENCE: 50

Gly His Arg Pro Leu Xaa Ile Ser Gly Gly
1               5                   10

<210> SEQ ID NO 51
<211> LENGTH: 10
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ambc

<400> SEQUENCE: 51

Gly His Arg Pro Leu Xaa Ile Ser Gly Gly
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ampa

<400> SEQUENCE: 52

Gly His Arg Pro Leu Xaa Ile Ser Gly Gly
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Anc

<400> SEQUENCE: 53

Gly His Arg Pro Leu Xaa Ile Ser Gly Gly
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Atpc

<400> SEQUENCE: 54

Gly His Arg Pro Leu Xaa Ile Ser Gly Gly
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 2-Atc
```

```
<400> SEQUENCE: 55

Gly His Arg Pro Leu Xaa Ile Ser Gly Gly
1               5                   10

<210> SEQ ID NO 56
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Acbt

<400> SEQUENCE: 56

Gly His Arg Pro Leu Xaa Ile Ser Gly Gly
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Acbo

<400> SEQUENCE: 57

Gly His Arg Pro Leu Xaa Ile Ser Gly Gly
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 1-Acmb

<400> SEQUENCE: 58

Gly His Arg Pro Leu Xaa Ile Ser Gly Gly
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 2-Acmb

<400> SEQUENCE: 59

Gly His Arg Pro Leu Xaa Ile Ser Gly Gly
1               5                   10

<210> SEQ ID NO 60
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Acmv

<400> SEQUENCE: 60

Gly His Arg Pro Leu Xaa Ile Ser Gly Gly
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Acq

<400> SEQUENCE: 61

Gly His Arg Pro Leu Xaa Ile Ser Gly Gly
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Accb

<400> SEQUENCE: 62

Gly His Arg Pro Leu Xaa Ile Ser Gly Gly
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Acpb

<400> SEQUENCE: 63

Gly His Arg Pro Leu Xaa Ile Ser Gly Gly
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (6)..(6)
<223> OTHER INFORMATION: PBD

<400> SEQUENCE: 64

Gly His Arg Pro Leu Xaa Ile Ser Gly Gly
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: ppp

<400> SEQUENCE: 65

Gly His Arg Pro Leu Xaa Ile Ser Gly Gly
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Cptd

<400> SEQUENCE: 66

Gly His Arg Pro Leu Xaa Ile Ser Gly Gly
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Thc

<400> SEQUENCE: 67

Gly His Arg Pro Leu Xaa Ile Ser Gly Gly
1               5                   10

<210> SEQ ID NO 68
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: bhc

<400> SEQUENCE: 68

Gly His Arg Pro Leu Xaa Ile Ser Gly Gly
1               5                   10
```

```
<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Accl

<400> SEQUENCE: 69

Gly His Arg Pro Leu Xaa Ser Gly Gly
1               5

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: PLSP

<400> SEQUENCE: 70

Gly His Arg Pro Leu Xaa Ile Ser Gly Gly
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: BTD

<400> SEQUENCE: 71

Gly His Arg Pro Leu Xaa Ile Ser Gly Gly
1               5                   10

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Gly His Arg Pro Pro Ile Ser Gly Gly
1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: hydroxyproline
```

```
<400> SEQUENCE: 73

Gly His Arg Pro Xaa Ile Ser Gly Gly
1               5

<210> SEQ ID NO 74
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: O-benzyl-hydroxyproline

<400> SEQUENCE: 74

Gly His Arg Pro Xaa Ile Ser Gly Gly
1               5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: O-t-butyl-hydroxyproline

<400> SEQUENCE: 75

Gly His Arg Pro Xaa Ile Ser Gly Gly
1               5

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: O-2-naphtyl-hydroxyproline

<400> SEQUENCE: 76

Gly His Arg Pro Xaa Ile Ser Gly Gly
1               5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: O-2-naphtyl-methyl-hydroxyproline

<400> SEQUENCE: 77

Gly His Arg Pro Xaa Ile Ser Gly Gly
1               5

<210> SEQ ID NO 78
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: O-phenyl-hydroxyproline

<400> SEQUENCE: 78

Gly His Arg Pro Xaa Ile Ser Gly Gly
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 4-(4-phenyl-benzyl-hydroxyproline)

<400> SEQUENCE: 79

Gly His Arg Pro Xaa Ile Ser Gly Gly
1               5

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: cis-3-phenyl-proline

<400> SEQUENCE: 80

Gly His Arg Pro Xaa Ile Ser Gly Gly
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: cis-4-phenyl-proline

<400> SEQUENCE: 81

Gly His Arg Pro Xaa Ile Ser Gly Gly
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (5)..(5)
<223> OTHER INFORMATION: trans-4-phenyl-proline

<400> SEQUENCE: 82

Gly His Arg Pro Xaa Ile Ser Gly Gly
1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: cis-5-phenyl-proline

<400> SEQUENCE: 83

Gly His Arg Pro Xaa Ile Ser Gly Gly
1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: trans-5-phenyl-proline

<400> SEQUENCE: 84

Gly His Arg Pro Xaa Ile Ser Gly Gly
1               5

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 4-benzyl-proline

<400> SEQUENCE: 85

Gly His Arg Pro Xaa Ile Ser Gly Gly
1               5

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 4-(4-bromobenzyl)-proline

<400> SEQUENCE: 86

Gly His Arg Pro Xaa Ile Ser Gly Gly
1               5
```

```
<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 4-cyclohexyl-proline

<400> SEQUENCE: 87

Gly His Arg Pro Xaa Ile Ser Gly Gly
1               5

<210> SEQ ID NO 88
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 4-fluoro-proline

<400> SEQUENCE: 88

Gly His Arg Pro Xaa Ile Ser Gly Gly
1               5

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Tic

<400> SEQUENCE: 89

Gly His Arg Pro Xaa Ile Ser Gly Gly
1               5

<210> SEQ ID NO 90
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: SSS
<220> FEATURE:
<221> NAME/KEY: MOD_RES
<222> LOCATION: (6)..(6)
<223> OTHER INFORMATION: Oic

<400> SEQUENCE: 90

Gly His Arg Pro Xaa Xaa Ile Ser Gly Gly
1               5                   10

<210> SEQ ID NO 91
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: SSS
<220> FEATURE:
<221> NAME/KEY: MOD_RES
<222> LOCATION: (6)..(6)
<223> OTHER INFORMATION: 1-aza-bicylco[3.3.0]bicyclooctan-carboxyl

<400> SEQUENCE: 91

Gly His Arg Pro Xaa Xaa Ile Ser Gly Gly
1               5                   10

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: cis-Acpc

<400> SEQUENCE: 92

Gly His Arg Pro Xaa Ile Ser Gly Gly
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: (1R,2R)-Acpc

<400> SEQUENCE: 93

Gly His Arg Pro Xaa Ile Ser Gly Gly
1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: (1S,2S)-Acpc

<400> SEQUENCE: 94

Gly His Arg Pro Xaa Ile Ser Gly Gly
1               5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (5)..(5)
<223> OTHER INFORMATION: 1-Acha

<400> SEQUENCE: 95

Gly His Arg Pro Xaa Ile Ser Gly Gly
1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Acpo

<400> SEQUENCE: 96

Gly His Arg Pro Xaa Ile Ser Gly Gly
1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 1-Acbc

<400> SEQUENCE: 97

Gly His Arg Pro Xaa Ile Ser Gly Gly
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Acpo

<400> SEQUENCE: 98

Gly His Arg Pro Xaa Ile Ser Gly Gly
1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 1-Achc

<400> SEQUENCE: 99

Gly His Arg Pro Xaa Ile Ser Gly Gly
```

```
1               5

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: (1R,2S)-2-Achc

<400> SEQUENCE: 100

Gly His Arg Pro Xaa Ile Ser Gly Gly
1               5

<210> SEQ ID NO 101
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: (1S,2R)-2-Achc

<400> SEQUENCE: 101

Gly His Arg Pro Xaa Ile Ser Gly Gly
1               5

<210> SEQ ID NO 102
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: (1S,2S)-2-Achc

<400> SEQUENCE: 102

Gly His Arg Pro Xaa Ile Ser Gly Gly
1               5

<210> SEQ ID NO 103
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 1-Acpec

<400> SEQUENCE: 103

Gly His Arg Pro Xaa Ile Ser Gly Gly
1               5

<210> SEQ ID NO 104
<211> LENGTH: 9
<212> TYPE: PRT
<213> ORGANISM: Artificial Sequence
<220> FEATURE:
```

-continued

```
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 1-Acprc

<400> SEQUENCE: 104

Gly His Arg Pro Xaa Ile Ser Gly Gly
1               5

<210> SEQ ID NO 105
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Aedfp

<400> SEQUENCE: 105

Gly His Arg Pro Xaa Ile Ser Gly Gly
1               5

<210> SEQ ID NO 106
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 1-Aic

<400> SEQUENCE: 106

Gly His Arg Pro Xaa Ile Ser Gly Gly
1               5

<210> SEQ ID NO 107
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 2-Aic

<400> SEQUENCE: 107

Gly His Arg Pro Xaa Ile Ser Gly Gly
1               5

<210> SEQ ID NO 108
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ambc

<400> SEQUENCE: 108
```

Gly His Arg Pro Xaa Ile Ser Gly Gly
1               5

<210> SEQ ID NO 109
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ampa

<400> SEQUENCE: 109

Gly His Arg Pro Xaa Ile Ser Gly Gly
1               5

<210> SEQ ID NO 110
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Asp
<220> FEATURE:
<221> NAME/KEY: MOD_RES
<222> LOCATION: (8)..(8)
<223> OTHER INFORMATION: Anc

<400> SEQUENCE: 110

Gly His Arg Pro Leu Xaa Lys Xaa Ile Ser Gly Gly
1               5                   10

<210> SEQ ID NO 111
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Atpc

<400> SEQUENCE: 111

Gly His Arg Pro Xaa Ile Ser Gly Gly
1               5

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 2-Atc

<400> SEQUENCE: 112

Gly His Arg Pro Xaa Ile Ser Gly Gly
1               5

```
<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Acbt

<400> SEQUENCE: 113

Gly His Arg Pro Xaa Ile Ser Gly Gly
1               5

<210> SEQ ID NO 114
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Acbo

<400> SEQUENCE: 114

Gly His Arg Pro Xaa Ile Ser Gly Gly
1               5

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 1-Acmb

<400> SEQUENCE: 115

Gly His Arg Pro Xaa Ile Ser Gly Gly
1               5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 2-Acmb

<400> SEQUENCE: 116

Gly His Arg Pro Xaa Ile Ser Gly Gly
1               5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (5)..(5)
<223> OTHER INFORMATION: Acmv

<400> SEQUENCE: 117

Gly His Arg Pro Xaa Ile Ser Gly Gly
1               5

<210> SEQ ID NO 118
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Acq

<400> SEQUENCE: 118

Gly His Arg Pro Xaa Ile Ser Gly Gly
1               5

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Accb

<400> SEQUENCE: 119

Gly His Arg Pro Xaa Ile Ser Gly Gly
1               5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Acpb

<400> SEQUENCE: 120

Gly His Arg Pro Xaa Ile Ser Gly Gly
1               5

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: PBD

<400> SEQUENCE: 121

Gly His Arg Pro Xaa Ile Ser Gly Gly
```

```
<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Bppp

<400> SEQUENCE: 122

Gly His Arg Pro Xaa Ile Ser Gly Gly
1               5

<210> SEQ ID NO 123
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Cptd

<400> SEQUENCE: 123

Gly His Arg Pro Xaa Ile Ser Gly Gly
1               5

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Thc

<400> SEQUENCE: 124

Gly His Arg Pro Xaa Ile Ser Gly Gly
1               5

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Abhc

<400> SEQUENCE: 125

Gly His Arg Pro Xaa Ile Ser Gly Gly
1               5

<210> SEQ ID NO 126
<211> LENGTH: 8
<212> TYPE: PRT
<213> ORGANISM: Artificial Sequence
<220> FEATURE:
```

-continued

```
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Acc1

<400> SEQUENCE: 126

Gly His Arg Pro Xaa Ser Gly Gly
1               5

<210> SEQ ID NO 127
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: PLSP

<400> SEQUENCE: 127

Gly His Arg Pro Xaa Ile Ser Gly Gly
1               5

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: BTD

<400> SEQUENCE: 128

Gly His Arg Pro Xaa Ile Ser Gly Gly
1               5

<210> SEQ ID NO 129
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: (1S,2R)Achc

<400> SEQUENCE: 129

Gly His Arg Pro Xaa Ile Ser Gly Gly
1               5

<210> SEQ ID NO 130
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
```

```
<222> LOCATION: (6)..(6)
<223> OTHER INFORMATION: Acdn

<400> SEQUENCE: 130

Gly His Arg Pro Leu Xaa Ile Ser Gly Gly
1               5                   10

<210> SEQ ID NO 131
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 131

Gly His Arg Pro Pro Ile Ser Gly Gly
1               5

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: hydroxyproline

<400> SEQUENCE: 132

Gly His Arg Pro Xaa Ile Ser Gly Gly
1               5

<210> SEQ ID NO 133
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (6)..(6)
<223> OTHER INFORMATION: O-benzyl-hydroxyproline

<400> SEQUENCE: 133

Gly His Arg Pro Leu Xaa Ile Ser Gly Gly
1               5                   10

<210> SEQ ID NO 134
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (6)..(6)
<223> OTHER INFORMATION: O-t-butyl-hydroxyproline

<400> SEQUENCE: 134
```

```
Gly His Arg Pro Leu Xaa Ile Ser Gly Gly
1               5                   10

<210> SEQ ID NO 135
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: O-2-naphtyl-hydroxyproline

<400> SEQUENCE: 135

Gly His Arg Pro Xaa Ile Ser Gly Gly
1               5

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: O-2-naphtyl-methyl-hydroxyproline

<400> SEQUENCE: 136

Gly His Arg Pro Xaa Ile Ser Gly Gly
1               5

<210> SEQ ID NO 137
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (6)..(6)
<223> OTHER INFORMATION: O-phenyl-hydroxyproline

<400> SEQUENCE: 137

Gly His Arg Pro Leu Xaa Ile Ser Gly Gly
1               5                   10

<210> SEQ ID NO 138
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: 4-phenyl-benzyl-proline

<400> SEQUENCE: 138
```

```
Gly His Arg Pro Xaa Ile Ser Gly Gly
1               5

<210> SEQ ID NO 139
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: cis-3-phenyl-proline

<400> SEQUENCE: 139

Gly His Arg Pro Xaa Ile Ser Gly Gly
1               5

<210> SEQ ID NO 140
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (6)..(6)
<223> OTHER INFORMATION: cis-4-phenyl-proline

<400> SEQUENCE: 140

Gly His Arg Pro Leu Xaa Ile Ser Gly Gly
1               5                   10

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: trans-4-phenyl-proline

<400> SEQUENCE: 141

Gly His Arg Pro Xaa Ile Ser Gly Gly
1               5

<210> SEQ ID NO 142
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (6)..(6)
<223> OTHER INFORMATION: cis-5-phenyl-proline

<400> SEQUENCE: 142
```

```
Gly His Arg Pro Leu Xaa Ile Ser Gly Gly
1               5                   10

<210> SEQ ID NO 143
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: trans-5-phenyl-proline

<400> SEQUENCE: 143

Gly His Arg Pro Xaa Ile Ser Gly Gly
1               5

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: 4-benzyl-proline

<400> SEQUENCE: 144

Gly His Arg Pro Xaa Ile Ser Gly Gly
1               5

<210> SEQ ID NO 145
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: 4-(4-bromobenzyl)-proline

<400> SEQUENCE: 145

Gly His Arg Pro Xaa Ile Ser Gly Gly
1               5

<210> SEQ ID NO 146
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (6)..(6)
<223> OTHER INFORMATION: 4-cyclohexyl-proline

<400> SEQUENCE: 146
```

```
Gly His Arg Pro Ala Xaa Ile Ser Gly Gly
1               5                   10

<210> SEQ ID NO 147
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (6)..(6)
<223> OTHER INFORMATION: 4-fluoro-proline

<400> SEQUENCE: 147

Gly His Arg Pro Ile Xaa Ile Ser Gly Gly
1               5                   10

<210> SEQ ID NO 148
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (6)..(6)
<223> OTHER INFORMATION: Asp
<220> FEATURE:
<221> NAME/KEY: MOD_RES
<222> LOCATION: (8)..(8)
<223> OTHER INFORMATION: Tic

<400> SEQUENCE: 148

Gly His Arg Pro Leu Xaa Lys Xaa Ile Ser Gly Gly Gly Tyr Arg
1               5                   10                  15

<210> SEQ ID NO 149
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: SSS
<220> FEATURE:
<221> NAME/KEY: MOD_RES
<222> LOCATION: (6)..(6)
<223> OTHER INFORMATION: Oic

<400> SEQUENCE: 149

Gly His Arg Pro Xaa Xaa Ile Ser Gly Gly
1               5                   10

<210> SEQ ID NO 150
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: SSS
<220> FEATURE:
<221> NAME/KEY: MOD_RES
<222> LOCATION: (6)..(6)
<223> OTHER INFORMATION: 1-aza-bicyclo[3.3.0]bicyclooctan-carboxyl

<400> SEQUENCE: 150

Gly His Arg Pro Xaa Xaa Ile Ser Gly Gly
1               5                   10

<210> SEQ ID NO 151
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (6)..(6)
<223> OTHER INFORMATION: cis-Acpc

<400> SEQUENCE: 151

Gly His Arg Pro Ala Xaa Ile Ser Gly Gly
1               5                   10

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: (1R,2R)-Acpc

<400> SEQUENCE: 152

Gly His Arg Pro Xaa Ile Ser Gly Gly
1               5

<210> SEQ ID NO 153
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (6)..(6)
<223> OTHER INFORMATION: (1S,2S)-Acpc

<400> SEQUENCE: 153

Gly His Arg Pro Leu Xaa Ile Ser Gly Gly
1               5                   10

<210> SEQ ID NO 154
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (6)..(6)
<223> OTHER INFORMATION: 1-Acha

<400> SEQUENCE: 154

Gly His Arg Pro Ile Xaa Ile Ser Gly Gly
1               5                   10

<210> SEQ ID NO 155
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: Acpo

<400> SEQUENCE: 155

Gly His Arg Pro Xaa Ile Ser Gly Gly
1               5

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: 1-Acbc

<400> SEQUENCE: 156

Gly His Arg Pro Xaa Ile Ser Gly Gly
1               5

<210> SEQ ID NO 157
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (6)..(6)
<223> OTHER INFORMATION: Acpo

<400> SEQUENCE: 157

Gly His Arg Pro Leu Xaa Ile Ser Gly Gly
1               5                   10

<210> SEQ ID NO 158
<211> LENGTH: 10
<212> TYPE: PRT
```

<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (6)..(6)
<223> OTHER INFORMATION: 1-Achc

<400> SEQUENCE: 158

Gly His Arg Pro Ala Xaa Ile Ser Gly Gly
1               5                   10

<210> SEQ ID NO 159
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: (1R,2S)-2-Achc

<400> SEQUENCE: 159

Gly His Arg Pro Xaa Ile Ser Gly Gly
1               5

<210> SEQ ID NO 160
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (6)..(6)
<223> OTHER INFORMATION: (1S,2R)-2-Achc

<400> SEQUENCE: 160

Gly His Arg Pro Val Xaa Ile Ser Gly Gly
1               5                   10

<210> SEQ ID NO 161
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: (1S,2S)-2-Achc

<400> SEQUENCE: 161

Gly His Arg Pro Xaa Ile Ser Gly
1               5

<210> SEQ ID NO 162
<211> LENGTH: 10
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (6)..(6)
<223> OTHER INFORMATION: 1-Acpec

<400> SEQUENCE: 162

Gly His Arg Pro Leu Xaa Ile Ser Gly Gly
1               5                   10

<210> SEQ ID NO 163
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: 1-Acprc

<400> SEQUENCE: 163

Gly His Arg Pro Xaa Ile Ser Gly Gly
1               5

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: Aedfp

<400> SEQUENCE: 164

Gly His Arg Pro Xaa Ile Ser Gly Gly
1               5

<210> SEQ ID NO 165
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (6)..(6)
<223> OTHER INFORMATION: 1-Aic

<400> SEQUENCE: 165

Gly His Arg Pro Val Xaa Ile Ser Gly Gly
1               5                   10

<210> SEQ ID NO 166
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: 2-Aic

<400> SEQUENCE: 166

Gly His Arg Pro Xaa Ile Ser Gly Gly
1               5

<210> SEQ ID NO 167
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (6)..(6)
<223> OTHER INFORMATION: Ambc

<400> SEQUENCE: 167

Gly His Arg Pro Leu Xaa Ile Ser Gly Gly
1               5                   10

<210> SEQ ID NO 168
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: Ampa

<400> SEQUENCE: 168

Gly His Arg Pro Xaa Ile Ser Gly Gly
1               5

<210> SEQ ID NO 169
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (6)..(6)
<223> OTHER INFORMATION: Anc

<400> SEQUENCE: 169

Gly His Arg Pro Ile Xaa Ile Ser Gly Gly
1               5                   10

<210> SEQ ID NO 170
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: Atpc

<400> SEQUENCE: 170

Gly His Arg Pro Xaa Ile Ser Gly Gly
1               5

<210> SEQ ID NO 171
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (6)..(6)
<223> OTHER INFORMATION: 2-Atc

<400> SEQUENCE: 171

Gly His Arg Pro Ala Xaa Ile Ser Gly Gly
1               5                   10

<210> SEQ ID NO 172
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (6)..(6)
<223> OTHER INFORMATION: Acbt

<400> SEQUENCE: 172

Gly His Arg Pro Leu Xaa Ile Ser Gly Gly
1               5                   10

<210> SEQ ID NO 173
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: Acbo

<400> SEQUENCE: 173

Gly His Arg Pro Xaa Ile Ser Gly Gly
1               5

<210> SEQ ID NO 174
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (6)..(6)
<223> OTHER INFORMATION: 1-Acmb

<400> SEQUENCE: 174

Gly His Arg Pro Leu Xaa Ile Ser Gly Gly
1               5                   10

<210> SEQ ID NO 175
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (6)..(6)
<223> OTHER INFORMATION: 2-Acmb

<400> SEQUENCE: 175

Gly His Arg Pro Leu Xaa Ile Ser Gly Gly
1               5                   10

<210> SEQ ID NO 176
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: Acmv

<400> SEQUENCE: 176

Gly His Arg Pro Xaa Ile Ser Gly Gly
1               5

<210> SEQ ID NO 177
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: Acq

<400> SEQUENCE: 177

Gly His Arg Pro Xaa Ile Ser Gly Gly
1               5

<210> SEQ ID NO 178
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (6)..(6)
<223> OTHER INFORMATION: Haic

<400> SEQUENCE: 178

Gly His Arg Pro Ala Xaa Ile Ser Gly Gly
1               5                   10

<210> SEQ ID NO 179
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: Accb

<400> SEQUENCE: 179

Gly His Arg Pro Xaa Ile Ser Gly Gly
1               5

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: Acpb

<400> SEQUENCE: 180

Gly His Arg Pro Xaa Ile Ser Gly Gly
1               5

<210> SEQ ID NO 181
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (6)..(6)
<223> OTHER INFORMATION: PBD

<400> SEQUENCE: 181

Gly His Arg Pro Leu Xaa Ile Ser Gly Gly
1               5                   10

<210> SEQ ID NO 182
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (6)..(6)
<223> OTHER INFORMATION: Bppp

<400> SEQUENCE: 182

Gly His Arg Pro Ala Xaa Ile Ser Gly Gly
1               5                   10

<210> SEQ ID NO 183
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: Cptd

<400> SEQUENCE: 183

Gly His Arg Pro Xaa Ile Ser Gly Gly
1               5

<210> SEQ ID NO 184
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (6)..(6)
<223> OTHER INFORMATION: Thc

<400> SEQUENCE: 184

Gly His Arg Pro Leu Xaa Ile Ser Gly Gly
1               5                   10

<210> SEQ ID NO 185
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: Abhc

<400> SEQUENCE: 185

Gly His Arg Pro Xaa Ile Ser Gly Gly
1               5

<210> SEQ ID NO 186
<211> LENGTH: 9
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (6)..(6)
<223> OTHER INFORMATION: Acc1

<400> SEQUENCE: 186

Gly His Arg Pro Ala Xaa Ser Gly Gly
1               5

<210> SEQ ID NO 187
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (6)..(6)
<223> OTHER INFORMATION: PLSP

<400> SEQUENCE: 187

Gly His Arg Pro Leu Xaa Ile Ser Gly Gly
1               5                   10

<210> SEQ ID NO 188
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
<220> FEATURE:
<221> NAME/KEY: MOD_RES
<222> LOCATION: (5)..(5)
<223> OTHER INFORMATION: BTD

<400> SEQUENCE: 188

Gly His Arg Pro Xaa Ile Ser Gly Gly
1               5

<210> SEQ ID NO 189
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: (1S,2R)Achc
<220> FEATURE:
<221> NAME/KEY: MOD_RES
<222> LOCATION: (10)..(10)
<223> OTHER INFORMATION: Cys-(S-succinimido-PEG20K)-amide

<400> SEQUENCE: 189

Gly His Arg Pro Xaa Ile Ser Gly Gly Cys
1               5                   10

<210> SEQ ID NO 190
```

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Acdn
<220> FEATURE:
<221> NAME/KEY: MOD_RES
<222> LOCATION: (10)..(10)
<223> OTHER INFORMATION: Cys-(S-succinimido-PEG20K)-amide

<400> SEQUENCE: 190

Gly His Arg Pro Xaa Ile Ser Gly Gly Cys
1               5                   10

<210> SEQ ID NO 191
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Cys-(S-succinimido-PEG20K)-amide

<400> SEQUENCE: 191

Gly His Arg Pro Pro Ile Ser Gly Gly Cys
1               5                   10

<210> SEQ ID NO 192
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: hydroxyproline
<220> FEATURE:
<221> NAME/KEY: MOD_RES
<222> LOCATION: (10)..(10)
<223> OTHER INFORMATION: Cys-(S-succinimido-PEG20K)-amide

<400> SEQUENCE: 192

Gly His Arg Pro Xaa Ile Ser Gly Gly Cys
1               5                   10

<210> SEQ ID NO 193
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: O-benzyl-hydroxyproline
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 193

Gly His Arg Pro Leu Xaa Ile Ser Gly Gly Cys
```

```
1               5                  10

<210> SEQ ID NO 194
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: O-t-butyl-hydroxyproline
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 194

Gly His Arg Pro Leu Xaa Ile Ser Gly Gly Cys
1               5                  10

<210> SEQ ID NO 195
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: O-2-naphtyl-hydroxyproline
<220> FEATURE:
<221> NAME/KEY: MOD_RES
<222> LOCATION: (10)..(10)
<223> OTHER INFORMATION: Cys-(S-succinimido-PEG20K)-amide

<400> SEQUENCE: 195

Gly His Arg Pro Xaa Ile Ser Gly Gly Cys
1               5                  10

<210> SEQ ID NO 196
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: O-2-naphtyl-methyl-hydroxyproline
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 196

Gly His Arg Pro Ala Xaa Ile Ser Gly Gly Cys
1               5                  10

<210> SEQ ID NO 197
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: O-phenyl-hydroxyproline
```

```
<220> FEATURE:
<221> NAME/KEY: MOD_RES
<222> LOCATION: (10)..(10)
<223> OTHER INFORMATION: Cys-(S-succinimido-PEG20K)-amide

<400> SEQUENCE: 197

Gly His Arg Pro Xaa Ile Ser Gly Gly Cys
1               5                   10

<210> SEQ ID NO 198
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 4-(4-phenyl-benzyl-proline)
<220> FEATURE:
<221> NAME/KEY: MOD_RES
<222> LOCATION: (10)..(10)
<223> OTHER INFORMATION: Cys-(S-succinimido-PEG20K)-amide

<400> SEQUENCE: 198

Gly His Arg Pro Xaa Ile Ser Gly Gly Cys
1               5                   10

<210> SEQ ID NO 199
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: cis-3-phenyl-proline
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 199

Gly His Arg Pro Ala Xaa Ile Ser Gly Gly Cys
1               5                   10

<210> SEQ ID NO 200
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: cis-4-phenyl-proline
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 200

Gly His Arg Pro Xaa Ile Ser Gly Gly Gly Cys
1               5                   10

<210> SEQ ID NO 201
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: trans-4-phenyl-proline
<220> FEATURE:
<221> NAME/KEY: MOD_RES
<222> LOCATION: (12)..(12)
<223> OTHER INFORMATION: Cys-(S-succinimido-PEG20K)-amide

<400> SEQUENCE: 201

Gly His Arg Pro Ala Xaa Ile Ser Gly Gly Gly Cys
1               5                   10

<210> SEQ ID NO 202
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: cis-5-phenyl-proline
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 202

Gly His Arg Pro Xaa Ile Ser Gly Gly Gly Cys
1               5                   10

<210> SEQ ID NO 203
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: trans-5-phenyl-proline
<220> FEATURE:
<221> NAME/KEY: MOD_RES
<222> LOCATION: (10)..(10)
<223> OTHER INFORMATION: Cys-(S-succinimido-PEG20K)-amide

<400> SEQUENCE: 203

Gly His Arg Pro Xaa Ile Ser Gly Gly Cys
1               5                   10

<210> SEQ ID NO 204
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 4-benzyl-proline
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 204
```

```
Gly His Arg Pro Xaa Ile Ser Gly Gly Gly Cys
1               5                   10
```

<210> SEQ ID NO 205
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 4-(4-bromobenzyl)-proline
<220> FEATURE:
<221> NAME/KEY: MOD_RES
<222> LOCATION: (12)..(12)
<223> OTHER INFORMATION: Cys-(S-succinimido-PEG20K)-amide

<400> SEQUENCE: 205

```
Gly His Arg Pro Leu Xaa Ile Ser Gly Gly Gly Cys
1               5                   10
```

<210> SEQ ID NO 206
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 4-cyclohexyl-proline
<220> FEATURE:
<221> NAME/KEY: MOD_RES
<222> LOCATION: (10)..(10)
<223> OTHER INFORMATION: Cys-(S-succinimido-PEG20K)-amide

<400> SEQUENCE: 206

```
Gly His Arg Pro Xaa Ile Ser Gly Gly Cys
1               5                   10
```

<210> SEQ ID NO 207
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 4-fluoro-proline
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 207

```
Gly His Arg Pro Xaa Ile Ser Gly Gly Gly Cys
1               5                   10
```

<210> SEQ ID NO 208
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (6)..(6)
<223> OTHER INFORMATION: Tic
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 208

Gly His Arg Pro Ala Xaa Ile Ser Gly Gly Cys
1               5                   10

<210> SEQ ID NO 209
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: SSS
<220> FEATURE:
<221> NAME/KEY: MOD_RES
<222> LOCATION: (6)..(6)
<223> OTHER INFORMATION: Oic
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 209

Gly His Arg Pro Xaa Xaa Ile Ser Gly Gly Cys
1               5                   10

<210> SEQ ID NO 210
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: SSS
<220> FEATURE:
<221> NAME/KEY: MOD_RES
<222> LOCATION: (6)..(6)
<223> OTHER INFORMATION: 1-aza-bicyclo[3.3.0]bicyclooctan-carboxyl
<220> FEATURE:
<221> NAME/KEY: MOD_RES
<222> LOCATION: (10)..(10)
<223> OTHER INFORMATION: Cys-(S-succinimido-PEG20K)-amide

<400> SEQUENCE: 210

Gly His Arg Pro Xaa Xaa Ile Ser Gly Cys
1               5                   10

<210> SEQ ID NO 211
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: cis-Acpc
<220> FEATURE:
<221> NAME/KEY: MOD_RES
<222> LOCATION: (11)..(11)
<223> OTHER INFORMATION: Cys-(S-succinimido-PEG20K)-amide
```

```
<400> SEQUENCE: 211

Gly His Arg Pro Ile Xaa Ile Ser Gly Gly Cys
1               5                   10

<210> SEQ ID NO 212
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: (1R,2R)-Acpc
<220> FEATURE:
<221> NAME/KEY: MOD_RES
<222> LOCATION: (10)..(10)
<223> OTHER INFORMATION: Cys-(S-succinimido-PEG20K)-amide

<400> SEQUENCE: 212

Gly His Arg Pro Xaa Ile Ser Gly Gly Cys
1               5                   10

<210> SEQ ID NO 213
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: (1S,2S)-Acpc
<220> FEATURE:
<221> NAME/KEY: MOD_RES
<222> LOCATION: (10)..(10)
<223> OTHER INFORMATION: Cys-(S-succinimido-PEG20K)-amide

<400> SEQUENCE: 213

Gly His Arg Pro Xaa Ile Ser Gly Gly Cys
1               5                   10

<210> SEQ ID NO 214
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 1-Acha
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 214

Gly His Arg Pro Leu Xaa Ile Ser Gly Gly Cys
1               5                   10

<210> SEQ ID NO 215
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (5)..(5)
<223> OTHER INFORMATION: Acpo
<220> FEATURE:
<221> NAME/KEY: MOD_RES
<222> LOCATION: (10)..(10)
<223> OTHER INFORMATION: Cys-(S-succinimido-PEG20K)-amide

<400> SEQUENCE: 215

Gly His Arg Pro Xaa Ile Ser Gly Gly Cys
1               5                   10

<210> SEQ ID NO 216
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 1-Acbc
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 216

Gly His Arg Pro Leu Xaa Ile Ser Gly Gly Cys
1               5                   10

<210> SEQ ID NO 217
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Acpo
<220> FEATURE:
<221> NAME/KEY: MOD_RES
<222> LOCATION: (10)..(10)
<223> OTHER INFORMATION: Cys-(S-succinimido-PEG20K)-amide

<400> SEQUENCE: 217

Gly His Arg Pro Xaa Ile Ser Gly Gly Cys
1               5                   10

<210> SEQ ID NO 218
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 1-Achc
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 218

Gly His Arg Pro Ala Xaa Ile Ser Gly Gly Cys
1               5                   10
```

```
<210> SEQ ID NO 219
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: (1R,2S)-2-Achc
<220> FEATURE:
<221> NAME/KEY: MOD_RES
<222> LOCATION: (10)..(10)
<223> OTHER INFORMATION: Cys-(S-succinimido-PEG20K)-amide

<400> SEQUENCE: 219

Gly His Arg Pro Xaa Ile Ser Gly Gly Cys
1               5                   10

<210> SEQ ID NO 220
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: (1S,2R)-2-Achc
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 220

Gly His Arg Pro Leu Xaa Ile Ser Gly Gly Cys
1               5                   10

<210> SEQ ID NO 221
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: (1S,2S)-2-Achc
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 221

Gly His Arg Pro Ala Xaa Ile Ser Gly Gly Cys
1               5                   10

<210> SEQ ID NO 222
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 1-Acpec
<220> FEATURE:
<221> NAME/KEY: MOD_RES
```

```
<222> LOCATION: (10)..(10)
<223> OTHER INFORMATION: Cys-(S-succinimido-PEG20K)-amide

<400> SEQUENCE: 222

Gly His Arg Pro Xaa Ile Ser Gly Gly Cys
1               5                   10

<210> SEQ ID NO 223
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: 1-Acprc
<220> FEATURE:
<221> NAME/KEY: MOD_RES
<222> LOCATION: (10)..(10)
<223> OTHER INFORMATION: Cys-(S-succinimido-PEG20K)-amide

<400> SEQUENCE: 223

Gly His Arg Pro Xaa Ile Ser Gly Gly Cys
1               5                   10

<210> SEQ ID NO 224
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Aedfp
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 224

Gly His Arg Pro Leu Xaa Ile Ser Gly Gly Cys
1               5                   10

<210> SEQ ID NO 225
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 1-Aic
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 225

Gly His Arg Pro Leu Xaa Ile Ser Gly Gly Cys
1               5                   10

<210> SEQ ID NO 226
<211> LENGTH: 11
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 2-Aic
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 226

Gly His Arg Pro Ala Xaa Ile Ser Gly Gly Cys
1               5                   10

<210> SEQ ID NO 227
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ambc
<220> FEATURE:
<221> NAME/KEY: MOD_RES
<222> LOCATION: (10)..(10)
<223> OTHER INFORMATION: Cys-(S-succinimido-PEG20K)-amide

<400> SEQUENCE: 227

Gly His Arg Pro Xaa Ile Ser Gly Gly Cys
1               5                   10

<210> SEQ ID NO 228
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ampa
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 228

Gly His Arg Pro Leu Xaa Ile Ser Gly Gly Cys
1               5                   10

<210> SEQ ID NO 229
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Anc
<220> FEATURE:
<221> NAME/KEY: MOD_RES
<222> LOCATION: (10)..(10)
<223> OTHER INFORMATION: Cys-(S-succinimido-PEG20K)-amide

<400> SEQUENCE: 229

Gly His Arg Pro Xaa Ile Ser Gly Gly Cys
```

```
<210> SEQ ID NO 230
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Atpc
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 230

Gly His Arg Pro Leu Xaa Ile Ser Gly Gly Cys
1               5                   10

<210> SEQ ID NO 231
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 2-Atc
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 231

Gly His Arg Pro Ile Xaa Ile Ser Gly Gly Cys
1               5                   10

<210> SEQ ID NO 232
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Acbt
<220> FEATURE:
<221> NAME/KEY: MOD_RES
<222> LOCATION: (10)..(10)
<223> OTHER INFORMATION: Cys-(S-succinimido-PEG20K)-amide

<400> SEQUENCE: 232

Gly His Arg Pro Xaa Ile Ser Gly Gly Cys
1               5                   10

<210> SEQ ID NO 233
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Acbo
```

```
<220> FEATURE:
<221> NAME/KEY: MOD_RES
<222> LOCATION: (10)..(10)
<223> OTHER INFORMATION: Cys-(S-succinimido-PEG20K)-amide

<400> SEQUENCE: 233

Gly His Arg Pro Xaa Ile Ser Gly Gly Cys
1               5                   10

<210> SEQ ID NO 234
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 1-Acmb
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 234

Gly His Arg Pro Ala Xaa Ile Ser Gly Gly Cys
1               5                   10

<210> SEQ ID NO 235
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: 2-Acmb
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 235

Gly His Arg Pro Lys Xaa Ile Ser Gly Gly Cys
1               5                   10

<210> SEQ ID NO 236
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Acmv
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 236

Gly His Arg Pro Leu Xaa Ile Ser Gly Gly Cys
1               5                   10

<210> SEQ ID NO 237
<211> LENGTH: 10
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Acq
<220> FEATURE:
<221> NAME/KEY: MOD_RES
<222> LOCATION: (10)..(10)
<223> OTHER INFORMATION: Cys-(S-succinimido-PEG20K)-amide

<400> SEQUENCE: 237

Gly His Arg Pro Xaa Ile Ser Gly Gly Cys
1               5                   10

<210> SEQ ID NO 238
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Haic
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 238

Gly His Arg Pro Leu Xaa Ile Ser Gly Gly Cys
1               5                   10

<210> SEQ ID NO 239
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Accb
<220> FEATURE:
<221> NAME/KEY: MOD_RES
<222> LOCATION: (10)..(10)
<223> OTHER INFORMATION: Cys-(S-succinimido-PEG20K)-amide

<400> SEQUENCE: 239

Gly His Arg Pro Xaa Ile Ser Gly Gly Cys
1               5                   10

<210> SEQ ID NO 240
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Acpb
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 240
```

```
Gly His Arg Pro Ala Xaa Ile Ser Gly Gly Cys
1               5                   10

<210> SEQ ID NO 241
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: PBD
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 241

Gly His Arg Pro Leu Xaa Ile Ser Gly Gly Cys
1               5                   10

<210> SEQ ID NO 242
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Bppp
<220> FEATURE:
<221> NAME/KEY: MOD_RES
<222> LOCATION: (10)..(10)
<223> OTHER INFORMATION: Cys-(S-succinimido-PEG20K)-amide

<400> SEQUENCE: 242

Gly His Arg Pro Xaa Ile Ser Gly Gly Cys
1               5                   10

<210> SEQ ID NO 243
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Cptd
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 243

Gly His Arg Pro Leu Xaa Ile Ser Gly Gly Cys
1               5                   10

<210> SEQ ID NO 244
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (5)..(5)
<223> OTHER INFORMATION: Thc
<220> FEATURE:
<221> NAME/KEY: MOD_RES
<222> LOCATION: (10)..(10)
<223> OTHER INFORMATION: Cys-(S-succinimido-PEG20K)-amide

<400> SEQUENCE: 244

Gly His Arg Pro Xaa Ile Ser Gly Gly Cys
1               5                   10

<210> SEQ ID NO 245
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Abhc
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 245

Gly His Arg Pro Leu Xaa Ile Ser Gly Gly Cys
1               5                   10

<210> SEQ ID NO 246
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Accl
<220> FEATURE:
<221> NAME/KEY: MOD_RES
<222> LOCATION: (10)..(10)
<223> OTHER INFORMATION: Cys-(S-succinimido-PEG20K)-amide

<400> SEQUENCE: 246

Gly His Arg Pro Xaa Ile Ser Gly Gly Cys
1               5                   10

<210> SEQ ID NO 247
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: PLSP
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 247

Gly His Arg Pro Ala Xaa Ile Ser Gly Gly Cys
1               5                   10

<210> SEQ ID NO 248
```

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: BTD
<220> FEATURE:
<221> NAME/KEY: MOD_RES
<222> LOCATION: (11)..(11)
<223> OTHER INFORMATION: Cys-(S-succinimido-PEG20K)-amide

<400> SEQUENCE: 248

Gly His Arg Pro Leu Xaa Ile Ser Gly Gly Cys
1               5                   10

<210> SEQ ID NO 249
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: (1S,2R)Achc
<220> FEATURE:
<221> NAME/KEY: MOD_RES
<222> LOCATION: (10)..(10)
<223> OTHER INFORMATION: Cys-(S-succinimido-PEG30K)-amide

<400> SEQUENCE: 249

Gly His Arg Pro Xaa Ile Ser Gly Gly Cys
1               5                   10

<210> SEQ ID NO 250
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: (1S,2R)Achc
<220> FEATURE:
<221> NAME/KEY: MOD_RES
<222> LOCATION: (11)..(11)
<223> OTHER INFORMATION: Cys-(S-succinimido-PEG40K)-amide

<400> SEQUENCE: 250

Gly His Arg Pro Leu Xaa Ile Ser Gly Gly Cys
1               5                   10

<210> SEQ ID NO 251
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Acdn
<220> FEATURE:
<221> NAME/KEY: MOD_RES
<222> LOCATION: (10)..(10)
<223> OTHER INFORMATION: Cys-(S-succinimido-PEG30K)-amide
```

```
<400> SEQUENCE: 251

Gly His Arg Pro Xaa Ile Ser Gly Gly Cys
1               5                   10

<210> SEQ ID NO 252
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Acdn
<220> FEATURE:
<221> NAME/KEY: MOD_RES
<222> LOCATION: (10)..(10)
<223> OTHER INFORMATION: Cys-(S-succinimido-PEG40K)-amide

<400> SEQUENCE: 252

Gly His Arg Pro Xaa Ile Ser Gly Gly Cys
1               5                   10

<210> SEQ ID NO 253
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(15)
<223> OTHER INFORMATION: Any amino acid
<220> FEATURE:
<221> NAME/KEY: MOD_RES
<222> LOCATION: (16)..(16)
<223> OTHER INFORMATION: Any amino acid or absent
<220> FEATURE:
<223> OTHER INFORMATION: see specification as filed for detailed
      description of substitutions and preferred embodiments

<400> SEQUENCE: 253

Gly His Arg Pro Xaa Xaa Xaa Xaa Xaa Xaa Xaa Xaa Xaa Xaa Xaa Xaa
1               5                   10                  15
```